US011410754B2

(12) United States Patent
Ishikawa et al.

(10) Patent No.: US 11,410,754 B2
(45) Date of Patent: Aug. 9, 2022

(54) CLOUD-TO-LOCAL, LOCAL-TO-CLOUD SWITCHING AND SYNCHRONIZATION OF MEDICAL IMAGES AND DATA

(71) Applicant: Konica Minolta Healthcare Americas, Inc., Wayne, NJ (US)

(72) Inventors: Takayuki Ishikawa, Wayne, NJ (US); Takao Shiibashi, Wayne, NJ (US)

(73) Assignee: Konica Minolta Healthcare Americas, Inc., Wayne, NJ (US)

( * ) Notice: Subject to any disclaimer, the term of this patent is extended or adjusted under 35 U.S.C. 154(b) by 708 days.

(21) Appl. No.: 15/476,445

(22) Filed: Mar. 31, 2017

(65) Prior Publication Data

US 2018/0285529 A1    Oct. 4, 2018

(51) Int. Cl.
*G16H 10/60*    (2018.01)
*G16H 30/20*    (2018.01)
*G16H 40/63*    (2018.01)

(52) U.S. Cl.
CPC ............. *G16H 10/60* (2018.01); *G16H 30/20* (2018.01); *G16H 40/63* (2018.01)

(58) Field of Classification Search
CPC .. G06Q 50/22–24; G16H 10/60; G16H 30/20; G16H 40/63; G06F 16/00; G06F 16/27; G06F 16/275

(Continued)

(56) References Cited

U.S. PATENT DOCUMENTS 7,234,033 B2 *   6/2007   Watanabe ........... G06F 11/2058
710/52

8,065,166 B2 *   11/2011   Maresh ................. G06F 19/321
705/3

(Continued)

FOREIGN PATENT DOCUMENTS

CN          105389463 B   * 11/2017
JP          2002-269243 A    9/2002
JP             5555088 B2    7/2014

OTHER PUBLICATIONS

Lomotey, Richard et al.; Mobile Medical Data Synchronization on Cloud-Powered Middleware Platform; IEEE Transactions on Services Computing 9.5: 757-770. IEEE Computer Soc. (Sep. 2016-Oct. 2016) (Year: 2016).*

(Continued)

*Primary Examiner* — Hiep V Nguyen
(74) *Attorney, Agent, or Firm* — Osha Bergman Watanabe & Burton LLP

(57) ABSTRACT

A method to prevent conflict during synchronization of medical data between a cloud repository on a cloud server and a plurality of local repositories on a plurality of local servers of healthcare facilities connected to the cloud server is provided. The plurality of local servers includes a first local server and the plurality of local repositories includes a first local repository on the first local server. The method includes, in response to a connection between the first local server and the cloud server getting disconnected, causing the first local server to: access the first local repository instead of the cloud repository, determine whether local data is associated with a shared patient registered with more than one healthcare facility among the healthcare facilities connected to the cloud server, and prohibit alteration of the local data if the local data is associated with the shared patient.

18 Claims, 18 Drawing Sheets

(58) Field of Classification Search
USPC .............................................................. 705/2
See application file for complete search history.

(56) References Cited

U.S. PATENT DOCUMENTS

| | | | |
|---|---|---|---|
| 2003/0220821 A1 | 11/2003 | Walter et al. | |
| 2013/0191347 A1* | 7/2013 | Bensinger | G06F 11/1464 707/649 |
| 2014/0201144 A1* | 7/2014 | Vibhor | H04L 67/18 707/634 |
| 2015/0058287 A1* | 2/2015 | Zhang | H04L 67/10 707/610 |

OTHER PUBLICATIONS

Office Action issued in counterpart Japanese Patent Application No. JP2018-058001A dated Sep. 28, 2021 (8 pages).
NFS Bible by Brent Callaghan, Ch. 8 Implementation of NFS, 8.14.6. Disconnection and Reconnection, pp. 265-266 (5 pages).

* cited by examiner

300A

| Patent ID | Patient Name | Attributed Facility ID | Report Information | Image Information |
|---|---|---|---|---|
| 00001 | Manabu Yamada | CL1 | Pneumonia | Chest CT |
| 00201 | Kei Matsuyama | HS1 | Right Upper Arm Fracture | Right Arm X-ray |
| ..... | ......... | ..... | ......... | ......... |

| Edit Status | Patent ID | Patient Name | Attributed Facility ID | Common Patient ID | Report Information | Image Information |
|---|---|---|---|---|---|---|
| R | 00001 | Manabu Yamada | HS1 | N/A | Pneumonia | Chest CT |
| RWD | 00201 | Kei Matsuyama | CL1 | C001 | Right Upper Arm Fracture | Right Arm X-ray |
| ..... | ..... | ......... | ..... | ..... | ......... | ......... |

FIG. 3B

| Function Item | | | | |
|---|---|---|---|---|
| Classification | Large Item | Small Item | | Contents | Settings |
| Functional Item | 100 Connection Monitoring | 101 | Check the connection to cloud periodically | Periodically Monitor/Check if the application proxy server (APS) can connect to cloud properly | Monitor/Check Interval. Default 10 secs (System level) |
| | 200 Connection Error (Detection) | 201 | Timeout | Specify the timeout value for network connection | Timeout setting. Default 3 secs (System level) |
| | | 203 | Number of Failures | Detect as connection is lost with continuous number of timeouts or another general network error | Number of connection test failure to detect connection is lost. Default 3 times (System level) |
| | 300 Connection Error (Notification) | 301 | Notify the connection error | Notification is sent to all the local computers connected to the APS | |
| | | 302 | Display message to try to re-connect to the cloud server | Notification is sent to all the local computers connected to the APS and a message is displayed to inform user that reconnection attempts will be made for pre-defined time. The user cannot use the application while this message is displayed. The system will operate normally if network connection is recovered during this message is displayed, but the message 303 is displayed if recovery attempts fail. Example message: "Connection to the cloud server has been lost. System trying to re-connect to the cloud server." | Time setting to display this message. Default 20 secs (System level) |
| | | 303 | Display message to change the connection from cloud to local | Notification is sent to all the local computers connected to the APS and a message is displayed to inform the user that the connection will be switched from cloud to local. Example message: "Connection to the cloud server has been lost. System connects from cloud to local. Please depress the OK button to close the application. Otherwise the application is forcefully closed after xx seconds." | |
| | | 304 | Forced termination | The application is forcefully closed after the message is displayed and pre-defined time has passed | Timeout setting for application forced close. Default 60 secs (System level) |
| | | 305 | Application startup prohibition | Once the network failure occurs between cloud and APS and the application running on the local computer connected to the APS has not been closed with 303 or 304 logic, users on those local computers cannot start the application | |
| | 400 Change the connection from cloud to local | 401 | Change the connection from cloud to local | Once the network failure occurs on an APS and no application is running on the APS, the application automatically starts and login screen is displayed on the local computers on which the application was closed with 302 or 303 logic | |

FIG. 13A

| Functional Item | | | |
|---|---|---|---|
| | 500 Constrains while connected to the local | 501 Constrains while connected the local | Editing/modifying/deleting of the existing information is prohibited to avoid conflict. However, new data can be added.<br><br><Patient Screen><br>- User can add patient<br>- User can edit newly added patient<br>- User cannot edit any information for existing patient<br><br><Viewer/Report Screen><br>- User can open viewer screen<br>- User can operate viewer function but nothing is saved (ex.) annotation/measurement, window level, flip, rotate, zoom, etc.<br>- User can create new report<br>- User can edit newly added report<br>- User cannot edit existing report<br><br><Input Data><br>- System can get only image data (ex.) DICOM images, general images,<br>- System refuse to get other data (ex.) HL7 order, Labo/Vital data, etc.<br><br><Settings><br>- User cannot add/modify/delete any settings |
| | 600 Connection recovered | 601 Connection confirmation | Detect as connection is recovered with continuous number of connection test success |
| | | | Number of connection test success to detect connection is recovered. Default 2 times (System level) |
| | | 602 Notify the connection recoverd | Notification is sent to all the local computer connected to the APS and a message is displayed for user to notify the connection will be changed from local to cloud.<br>"Connection to the cloud server has been recovered. System connects from local to cloud. Please depress the OK button to close the application. Or, you can choose to continue to use application. The application is forcefully closed after xx seconds without selection."<br>* The data in middle of input is saved when application is closed. |
| | | 603 Forced termination | The application is forcefully closed after the message is displayed and then pre-defined time is passed<br>* The data in middle of input is saved when application is closed. |
| | | | Same as 602 |
| | | 604 Application startup prohibition | Once the network connection recover between cloud and APS and the application running on the local computer which is connected to the APS has not been closed with 602 or 603 logic, any user on those local computer cannot start the application |
| | | ⋮ | |

FIG. 13B

| Funtional Item | 700 | Switch the connection from local to cloud | 701 | Switch the connection from local to cloud | Once the network connection is recovered on an APS and no application is running on the APS, Application automatically starts on the local computers on which the application was closed with 602 or 603 logic. At this moment, the message "Synchronizing..." is displayed until the synchronization process is done, and user cannot execute or operate the application during that time. Once the synchronization process is done, then login screen is displayed |
|---|---|---|---|---|---|
| | 800 | Synchronization (Upload) | 801 | Synchronization between local and cloud | Once the network connection is recovered between local and cloud, synchronization process from local to cloud begin to update the information that is added on local side while the connection has been lost |

FIG. 13C

CLOUD-TO-LOCAL, LOCAL-TO-CLOUD SWITCHING AND SYNCHRONIZATION OF MEDICAL IMAGES AND DATA

BACKGROUND

Medical images and medical data play a crucial role in the diagnosis of a patient. Healthcare facilities (e.g., hospitals) have realized the benefits of electronically storing medical images and medical data. The digitalization of the medical images and data not only enables users to easily access medical images and medical data, but also enables the images and data to be easily shared between multiple healthcare facilities.

In the healthcare industry, the use of a system known as a Picture Archiving and Communications System ("PACS") is becoming increasing popular for convenient storage and access of medical images. Generally, PACS comprises a multitude of devices working cooperatively to digitally capture, store, manage, distribute, and display medical images generated by various imaging modalities, such as computed tomography (CT), magnetic resonance imaging (MRI), position emission tomography (PET), ultrasound, X-ray, etc. PACS allows various healthcare facilities to share all types of images captured internally or externally.

More recently, cloud-based PACS have emerged as a way to improve efficiency and accessibility of traditional PACS. In general, a "cloud" can be understood as an online storage system that provides remote, on-demand access of computing resources and data over the Internet to multiple computers and devices in various locations. Cloud-based PACS may be provided by vendors who use remote or off-site data centers in various locations for storage of medical images.

SUMMARY

In general, in one aspect, the invention relates to a method to prevent conflict during synchronization of medical data between a cloud repository on a cloud server and a plurality of local repositories on a plurality of local servers of healthcare facilities connected to the cloud server. The plurality of local servers comprises a first local server and the plurality of local repositories comprises a first local repository on the first local server. The method comprises: in response to a connection between the first local server and the cloud server getting disconnected, causing the first local server to: access the first local repository instead of the cloud repository, determine whether local data is associated with a shared patient registered with more than one healthcare facility among the healthcare facilities connected to the cloud server, and prohibit alteration of the local data if the local data is associated with the shared patient, wherein alteration of remote data on the cloud server that corresponds to the prohibited local data by any one of the other plurality of local servers is allowed.

In general, in one aspect, the invention relates to a non-transitory computer-readable medium (CRM) storing instructions that causes a first local server coupled to a computer to perform an operation to prevent conflict during synchronization of medical data a between a cloud repository on a cloud server and a plurality of local repositories on a plurality of local servers of healthcare facilities connected to the cloud server. The plurality of local servers comprises the first local server and the plurality of local repositories comprises a first local repository on the first local server. The operation comprises: in response to a connection between the first local server and the cloud server getting disconnected, causing the first local server to: access the first local repository instead of the cloud repository, determine whether local data is associated with a shared patient registered with more than one healthcare facility among the healthcare facilities connected to the cloud server, and prohibit alteration of the local data if the local data is associated with the shared patient, wherein alteration of a remote data on the cloud server that corresponds to the prohibited local data by any one of the other plurality of local servers is allowed.

In general, in one aspect, the invention relates to a system that prevents conflict during synchronization of medical data. The system comprises: a cloud server, a cloud repository on the cloud server, and a plurality of local repositories on a plurality of local servers of healthcare facilities connected to the cloud server. The plurality of local servers comprises a first local server and the plurality of local repositories comprises a first local repository on the first local server. In response to a connection between the first local server and the cloud server getting disconnected, causing the first local server to: access the first local repository instead of the cloud repository, determine whether local data is associated with a shared patient registered with more than one healthcare facility among the healthcare facilities connected to the cloud server, and prohibit alteration of the local data if the local data is associated with the shared patient, wherein alteration of a remote data on the cloud server that corresponds to the prohibited local data by any one of the other plurality of local servers is allowed.

Other aspects and advantages of the invention will be apparent from the following description and the appended claims.

BRIEF DESCRIPTION OF DRAWINGS

FIGS. 3A and 3B show data tables in accordance with one or more embodiments.

FIGS. 13A, 13B, and 13C show an implementation example in accordance with one or more embodiments.

DETAILED DESCRIPTION

Figure 1A:
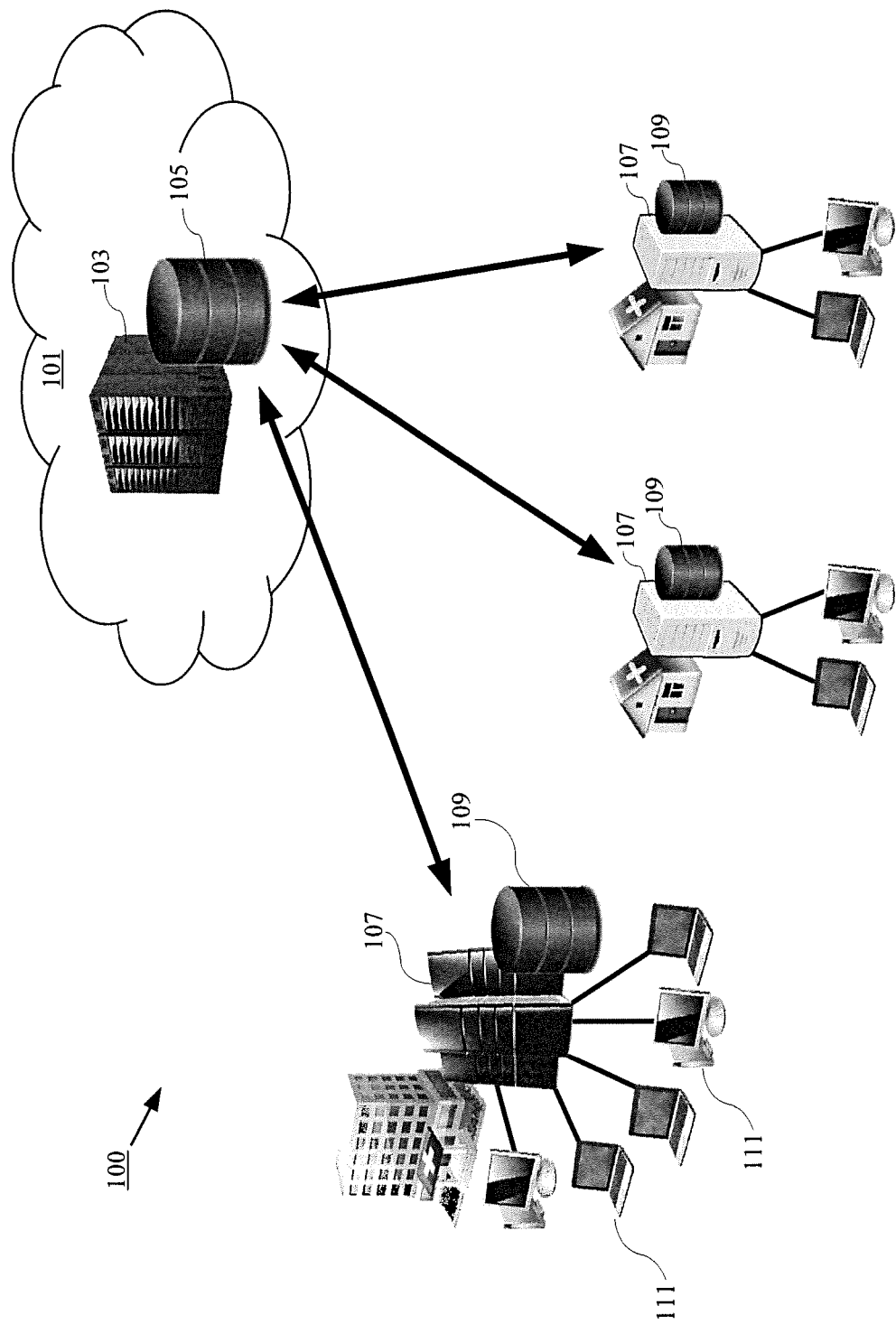
FIGS. 1A and 1B show a system in accordance with one or more embodiments.

Specific embodiments will now be described in detail with reference to the accompanying figures. Like elements in the various figures are denoted by like reference numerals for consistency. Like elements may not be labeled in all figures for the sake of simplicity.

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers does not imply or create a particular ordering of the elements or limit any element to being only a single element unless expressly disclosed, such as by the use of the terms "before," "after," "single," and other such terminology. Rather, the use of ordinal numbers is to distinguish between the elements. By way of an example, a first element is distinct from a second element, and the first element may encompass more than one element and succeed (or precede) the second element in an ordering of elements.

It is to be understood that the singular forms "a," "an," and "the" include plural referents unless the context clearly dictates otherwise. Thus, for example, reference to "a horizontal beam" includes reference to one or more of such beams.

Terms such as "approximately," "substantially," etc., mean that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

It is to be understood that, one or more of the steps shown in the flowcharts may be omitted, repeated, and/or performed in a different order than the order shown. Accordingly, the scope of the invention should not be considered limited to the specific arrangement of steps shown in the flowcharts.

Although multiple dependent claims are not introduced, it would be apparent to one of ordinary skill that the subject matter of the dependent claims of one or more embodiments may be combined with other dependent claims.

In general, one or more embodiments of the invention provide a method, a non-transitory computer readable medium, and a system configured for cloud-to-local, local-to-cloud switching and synchronization of medical images and data with a mechanism to prevent conflict during synchronization. A "conflict" generally refers to a disagreement or incompatibility that occurs between medical images and data during synchronization. The cloud-based PACS in accordance with one or more embodiments enables all healthcare facilities that are given permission to access a cloud data repository or database ("cloud repository"), such as facilities within the same hospital group, to share medical images and data. The medical images and data may also include a patient's medical reports. For example, a healthcare facility would be able to access and retrieve its patients' medical images and data obtained at the other healthcare facilities that are "in-network" (i.e., having permission to access the same portion of the cloud repository). Specifically, according to one or more embodiments, in-network healthcare facilities can more effectively utilize cloud-based PACS to share and update medical images and data for patients who frequent more one or more of the in-network healthcare facilities (i.e., a shared or common patient between two or more in-network healthcare facilities).

Moreover, unlike conventional cloud-based PACS, one or more embodiments of the invention enable a healthcare facility that utilizes cloud-based PACS to remain operational even when a network connection between the healthcare facility and the cloud is disconnected and when an uploading or updating of data causes a conflict situation between multiple healthcare facilities. Specifically, in-network healthcare facilities that utilize one or more embodiments are able to automatically keep on-site or local data repositories or databases ("local repositories") updated with the most recent patient images and data stored in the cloud repository based on a need of the users of the cloud-based PACS (e.g., healthcare professionals). Further, the cloud-based PACs at each of the facilities are also provided with a mechanism to prevent conflict during synchronization. For example, if one facility updates or obtains a new medical image of a particular patient, the cloud repository may be automatically updated with the updated or new medical image, and all the local repositories of the in-network facilities that treat or care for that same patient may be automatically synchronized with the cloud repository.

In one or more embodiments, in the event of a loss of connection, the disconnected healthcare facilities automatically switch access to the local repositories instead of the cloud repository. This enables the healthcare facilities to establish a continuous workflow without experiencing any downtime caused by the disconnection from the network. Because the local repositories of in-network facilities are synchronized with the cloud repository, the facilities are able to at least temporarily access and work with the most up-to-date data, even without connection to the cloud. However, not all the data on the cloud repository need necessarily be synchronized. In one or more embodiments, the synchronization occurs only with respect to data that is necessary or is of interest to the respective facilities. For example, a facility may not want its local repository filled or local server burdened with medical images related to people who are not patients of that facility.

In one or more embodiments, medical data may be shared among multiple in-network healthcare facilities, but users at an in-network healthcare facility disconnected from the cloud are prohibited from altering (i.e., modifying or editing) shared medical data stored in local repositories of the disconnected in-network healthcare facility. This reduces the possibility of a conflict when the disconnected in-network healthcare facility synchronizes data with the cloud upon reconnecting with the cloud. For example, because users at the disconnected in-network healthcare facility cannot easily determine whether the shared data is being locally edited at another in-network healthcare facility, those users might also edit the same shared data. Therefore, a possibility arises where the two different in-network healthcare facilities both attempt to upload the separately edited shared data to the cloud, which would cause the conflict to occur. When a conflict occurs, the systems at the facilities that cause the conflict may be temporarily unavailable in order for the systems to properly resolve the conflict, which would result in unintended and unnecessary downtime for the users.

In one or more embodiments, the users at in-network healthcare facilities that are still connected to the cloud are prohibited from altering certain medical data stored in the cloud repository determined to be associated with an in-network healthcare facility that is disconnected from the cloud. This enables a further reduction in the possibility of a conflict when the disconnected in-network healthcare facility synchronizes data with the cloud upon reconnecting with the cloud. For example, because users at the connected in-network healthcare facilities cannot easily determine which medical data stored at the disconnected in-network healthcare facility are being edited, those users might edit medical data stored on the cloud that corresponds to the medical data edited locally at the disconnected in-network healthcare facility. Therefore, a possibility arises where the two different in-network healthcare facilities both attempt to update the separately edited medical data in the cloud, which would cause the conflict to occur.

In one or more embodiments, when the connection is reestablished, the medical images and data stored in the local repositories during the time of network disconnection are automatically uploaded to the cloud repository. This enables all of the other in-network healthcare facilities to update their respective local repositories with the most up-to-date medical images and data.

Figure 1B:
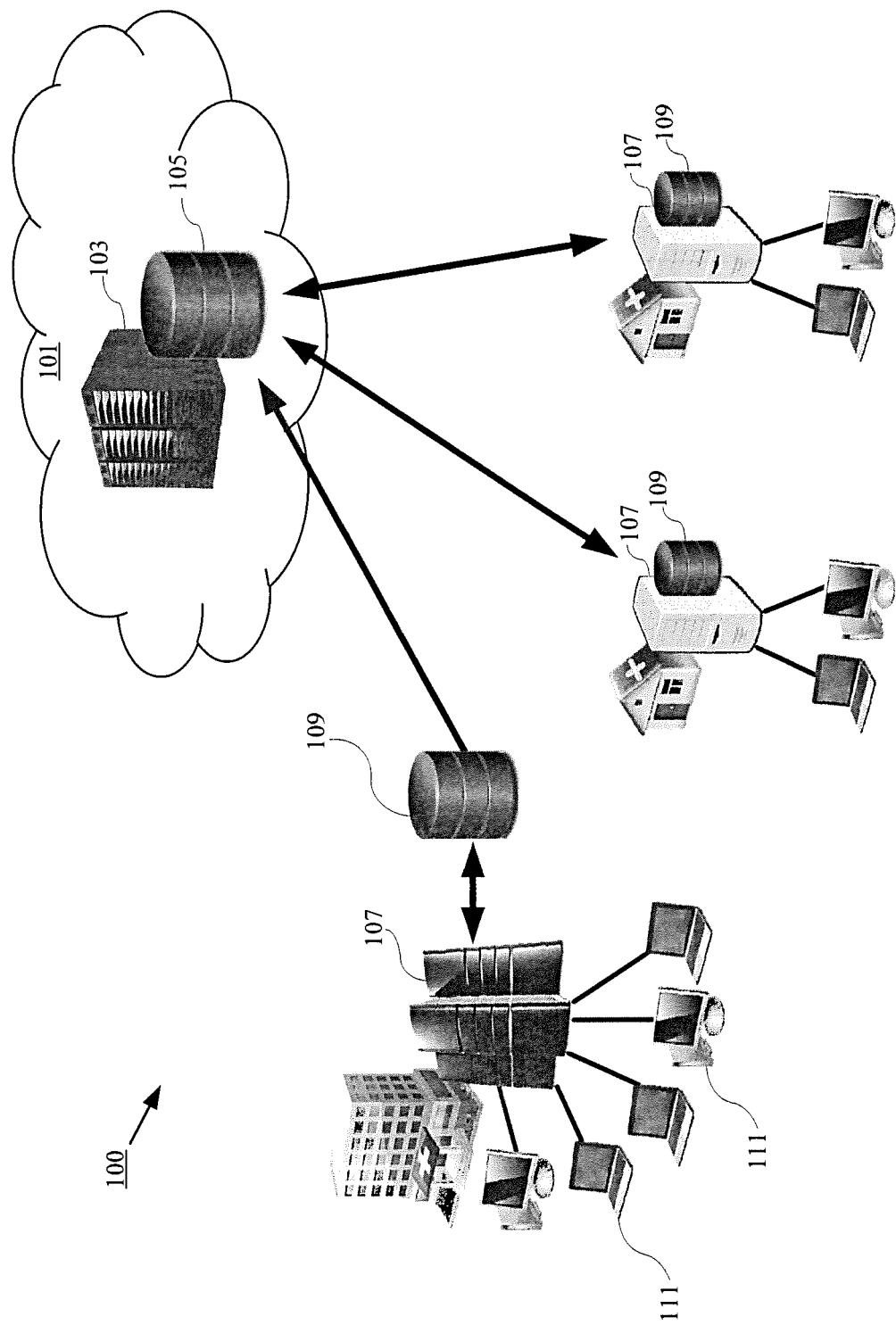

FIGS. 1A and 1B show a system (100) in accordance with one or more embodiments of the invention. As shown in FIGS. 1A and 1B, the system (100) includes a cloud (101) that includes a cloud server (103) with a cloud repository (105), and multiple local servers (107) (e.g., application proxy servers (APS)) and local repositories (109) associated with different in-network healthcare facilities (not labeled). The multiple local servers (107) are authorized to access/view the cloud server (103). In addition to the right to access the remote data on the cloud server (103), certain local servers (107) may also have the right to edit the remote data. Each of the healthcare facilities may be a type of facility that provides medical care such as a public hospital, a private hospital, a medical clinic, a dental clinic, etc.

As also shown in FIGS. 1A and 1B, each healthcare facility in the system (100) includes multiple user computing devices (111) (herein referred to as "a local computer") coupled to the local servers (107). Each local computer (111) may correspond to a personal computer (PC), a laptop, a mobile computing device (e.g., tablet PC, smartphone, etc.), a server, a mainframe, a kiosk, etc.

In one or more embodiments, the cloud server (103) with the cloud repository (105) may be operated by a vendor providing the cloud-based PACS or another third-party associated with such a vendor. In one or more embodiments, the cloud server (103) is a physical and/or virtual computing infrastructure that performs application and information processing. For example, the cloud server (103) may be a virtual server or a physical server accessed remotely via the Internet. In one or more embodiments, the cloud repository (105) is an online repository of data. For example, the cloud repository may be a virtual data room (VDR) or a database (or group of databases) accessed remotely via the Internet.

In one or more embodiments, the cloud server (103) is configured to receive the medical images and data transmitted from the local servers (107) and store the medical images and data in the cloud repository (105) as remote data.

In one or more embodiments, each local server (107) is operated by the associated healthcare facility. The local server (107) is configured to transmit the medical images and data received from the local computers (111) to the cloud repository (105) on the cloud server (103). Each local repository (109) is operated and maintained by the associated healthcare facility. The local repository (109) may locally store medical images and data received from the local server (107) and the cloud repository (105) local data.

In one or more embodiments, the local computers (111) are operated by medical professionals associated with the respective healthcare facilities and are configured to transmit to the local server (107) medical images and data taken from one or more modalities (not shown) in the healthcare facility. In one or more embodiments, the local computers (111) may be configured as the local server (107). In one or more embodiments, the local computers (111) may also include the local repository (109).

In one or more embodiments, the local computers are configured to store an application provided by the vendor that operates the cloud (101). In one or more embodiments, the application may be provided by a third-party associated with the vendor. The application may be an independent software application or a web-browser based application with a graphical user interface ("GUI") that allows the local computers (111) to access the cloud (101).

FIG. 1A shows an example in accordance with one or more embodiments where the connection between the in-network healthcare facilities and the cloud (101) is stable. In this state, the multiple in-network healthcare facilities may communicate bilaterally with the cloud (101). As shown in FIG. 1A, the in-network healthcare facilities may transmit locally-obtained medical images and data to the cloud (101) to be stored as remote data in the cloud repository (105) accessible to other in-network healthcare facilities. In one or more embodiments, the in-network healthcare facilities may retrieve medical images and data from the cloud (101) to be stored as local data in their respective local repositories (109).

In one or more embodiments, not all of the remote data stored in the cloud repository (105) need be retrieved by the in-network healthcare facilities to be stored as local data. The remote data to be retrieved and stored as local data may vary based on the size and need of the healthcare facility or on the preferences of the local computers (111) (e.g., healthcare professionals). For example, the remote data to be retrieved and stored as local data in the local repositories (109) of certain in-network healthcare facilities may be based on specific individuals who are patients of those facilities. Thus, if a particular individual is not a patient of a particular in-network healthcare facility, that healthcare facility may not retrieve and store that patient's medical images and data from the cloud (101) as local data. This option may be particularly useful for smaller healthcare facilities with smaller local servers (107) and local repositories (109) with limited storage and processing power. In one or more embodiments, the remote data to be retrieved and stored as local data in the local repositories (109) of certain in-network healthcare facilities may be based on a specific medical study, medical series, medical image, or medical report instead of being based on specific individuals who are patients of those facilities.

In one or more embodiments, users of the local computers (111) at each in-network healthcare facility may view the medical images and data stored on the cloud repository (105) through a web-browser based version of the application that is stored on the cloud server (103). The user may also view the images through a local version of the application stored on the local computers (111). For example, healthcare professionals may determine if any of the local data stored in the local repository (109) has been updated by another healthcare professional associated with a different in-network healthcare facility, and retrieve the updated data from the cloud repository (105) to replace the current local data. In one or more embodiments, the updating of the local data may be performed automatically by the system (100), e.g., through the application stored on the local computers (111).

For example, an individual may be a patient at multiple in-network healthcare facilities. Each of these in-network healthcare facilities may store the individual's medical images and data as local data. In one or more embodiments, the individual's medical images and data are updated in the cloud repository (105) by one of the in-network healthcare facilities, the other in-network healthcare facilities where the individual is also a patient may automatically retrieve (synchronize) the individual's updated images and data to keep the local data in the local repository (109) up-to-date. The automatic updating of the cloud repository (105) and/or synchronization of the pertinent local repositories (109) may be triggered every time the individual's medical images or data are updated on the cloud, or may be triggered at predetermined intervals.

FIG. 1B shows an example in accordance with one or more embodiments where a connection between one of the in-network healthcare facilities and the cloud (101) is disconnected. In this state, the application may automatically configure the local computers (111) and local servers (107) at the disconnected healthcare facility to access the local data stored in the local repository (109). In one or more embodiments, the disconnected healthcare facility continues to store into the local repository (109) medical images and data taken or updated during the time of disconnection. This enables the disconnected healthcare facility to establish a continuous workflow without experiencing any downtime caused by the disconnection from the cloud (101).

Then, when the connection between the disconnected healthcare facility is reestablished with the cloud (101), the local computers (111) and local servers (107) of the reconnected healthcare facility may be configured by the application to transmit to the cloud (101) all of the medical images and data stored in the local repository taken or updated during the time of disconnection. Such medical images and data may then be stored in the cloud repository (105) as new remote data. As the cloud (101) is being updated with the medical images and data from the reconnected healthcare facility, the application stored in the local computers (111) of the other in-network facilities may automatically update their respective local repositories (109) with the new remote data.

Figure 2A:
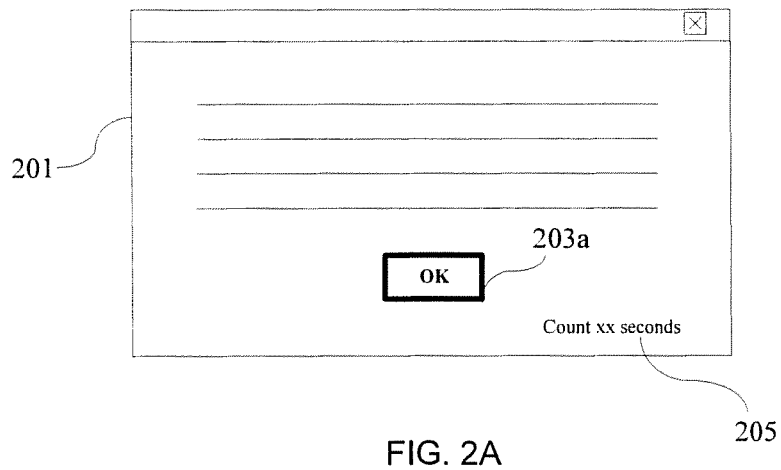
FIGS. 2A and 2B show a display message in accordance with one or more embodiments.
Figure 2B:
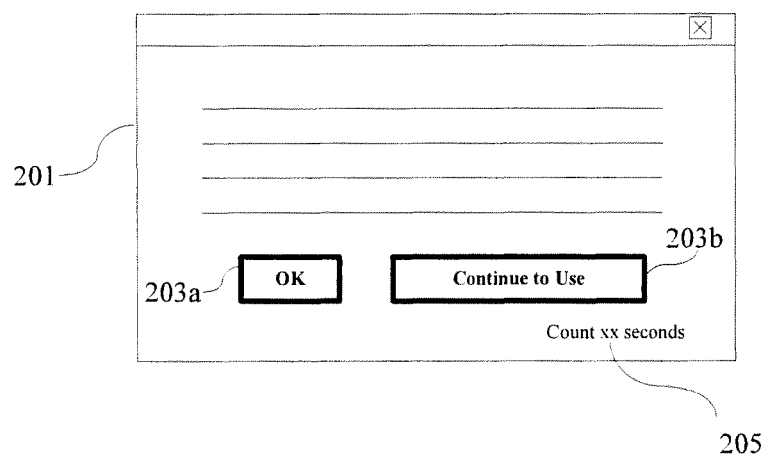

FIGS. 2A and 2B show a display message (201) in accordance with one or more embodiments, which may be displayed as part of a pop-up window by the application on the local computer (111) for its user. In this example, the display message (201) includes a user-selectable tab (203a and 203b) (e.g., selectable by the user with a click of a mouse) and a countdown timer (205). The display message (201) may appear as a pop-up window on a display of the local computer (111). The display message (201) may contain a message related to the current connection status between the local severs (107) of the in-network healthcare facilities and the cloud server (103).

FIG. 2A shows an example of the display message (201) when the connection between a local sever (107) of one of the in-network healthcare facilities and the cloud server (103) is disconnected. The display message (201) would include a message that indicates that the connection to the cloud (101) has been disconnected and that the local computer (111) will automatically access the local repository (109) when the countdown timer (205) runs out. Although a single local repository is used in certain descriptions herein for illustration purposes, the number of local computers and local repositories at each healthcare facility may vary.

In one or more embodiments, the users operating the local computer (111) may either wait for the countdown timer (205) to run out or directly click on the user-selectable tab (203a) to access the local repository (109) instead of the cloud repository (105) (i.e., switch access to the local repository (109)).

FIG. 2B shows an example of the display message (201) when the connection between a local sever (107) of one of the disconnected in-network healthcare facility and the cloud server (103) is reestablished. The display message (201) would include a message that indicates that the connection to the cloud (101) has been reestablished and prompts the user (e.g., healthcare professional) to choose between continuing to work off the local repository (109) or to re-access the cloud repository (105). In one or more embodiments, the application of the system (100) gives the user the option to work off the local repository only temporarily (e.g., for a pre-set or predetermined time period). In such a case, as shown in the example of FIG. 2B, the display message (201) may further include a message indicating that the local computer (111) would automatically re-access the cloud repository (105) when the countdown timer (205) runs out (i.e., switch access back to the cloud repository (105)).

Still referring to FIG. 2B, in one or more embodiments, the user may either select user-selectable tab (203a) to immediately re-access the network repository (105) or select user-selectable tab (203b) to continue to work locally off the local repository (109). Again, in this example, the continued use of the local repository after the connection with the cloud has been reestablished is limited. Once the pre-set time period has expired, the user would be prompted with another display message (201) to reconnect to the cloud (101).

FIGS. 3A and 3B show data tables (300A, 300B) in accordance with one or more embodiments, which may store patient related information that can be viewed and edited by the users of the local computer (111).

FIG. 3A shows an example of a data table (300A) that includes data associated with each medical image. In one or more embodiments, the data table (300A) may include patient related information such as, but not limited to, a Patient ID (301), Patient Name (303), Attributed Facility ID (305), Report Information (307), and Image Information (309).

In one or more embodiments, the Patient ID (301) is an individual's patient identification number. Each individual will have a single unique Patient ID (301). The individual's Patient ID (301) is shared among the in-network healthcare facilities. The Patient Name (303) is the legal name of the individual.

In one or more embodiments, the Attributed Facility ID (305) may be the identification number of the in-network healthcare facility where the individual is a patient (e.g., the in-network healthcare facility associated with the individual). In one or more embodiments, the Attributed Facility ID (305) may be the identification number of the in-network healthcare facility that obtained the first image of the particular patient uploaded onto the cloud (101), in which case the patient will have no more than one Attributed Facility ID (305). In one or more embodiments, the Attributed Facility ID may be assigned directly by a user at an in-network healthcare facility (i.e., a healthcare professional).

In one or more embodiments, the Report Information (307) includes information on the individual's medical diagnosis. The Image Information (309) includes a brief description of the medical image and the name of the modality used to generate the medical image.

FIG. 3B shows an example of a data table (300B) that includes data associated with each medical image. The data table (300B) includes the same data as the data table (300A) described in FIG. 3A, but further includes a Common Patient ID (306) and an Edit Status (304).

In one or more embodiments, the Common Patient ID (306) indicates that an individual is a shared patient between two or more of the multiple in-network healthcare facilities (i.e., the individual is a patient registered with at least two different in-network healthcare facilities). The Edit Status (304) is an identifier that indicates to the first local computer (111) whether the metadata of the respective medical data can be edited. For example, as shown in FIG. 3B, the Edit Status (304) "R" indicates that the metadata is "Read-Only" data that can only be viewed and not edited. The Edit Status (304) "RWD" (i.e., Read, Write, Delete) indicates that metadata is can be read, edited, and deleted (i.e., alteration of the medical data is possible).

In one or more embodiments, the data in data tables (300A, 300B) as shown in FIGS. 3A and 3B are embedded as metadata in the medical image, which may be a Digital Imaging and Communications in Medicine Format (DICOM-format) image. In one or more embodiments, DICOM may be the universal image format for implementing the system (100). The data from the tables (300A, 300B) can be extracted from the DICOM-format images using the application of one or more embodiments stored in the local computers (111). In one or more embodiments, the data in data tables (300A, 300B) may also be directly imbedded as metadata in the medical data, which can be either the patient's medical images or a patient's medical report.

The data in the tables (300A, 300B) may be sorted in any number of ways. In the example shown FIGS. 3A and 3B, the data is sorted by patient. However, the data can be sorted another way using any one of the patient related information based, for example, on the preferences of the healthcare professionals. Once the data from the data tables (300A and 300B) has been extracted from the medical image, healthcare professionals can edit/modify the data using the GUI provided with the application of one or more embodiments. In one or more embodiments, the extracted data tables (300A and 300B) are stored in the local servers (107).

FIGS. 4-7 show different states of the system of FIGS. 1A and 1B in accordance with one or more embodiments. The cloud (101), the cloud server (103), the cloud repository (105), the local servers (107), the local repository (109), the local computers (111), the display message (201), the user selectable tab(s) (203a and 203b), and the countdown timer (205) may be identical or substantially similar as described above with respect to FIGS. 1, 2A, and 2B. Detailed descriptions of such like components will not be repeated below.

Figure 4:
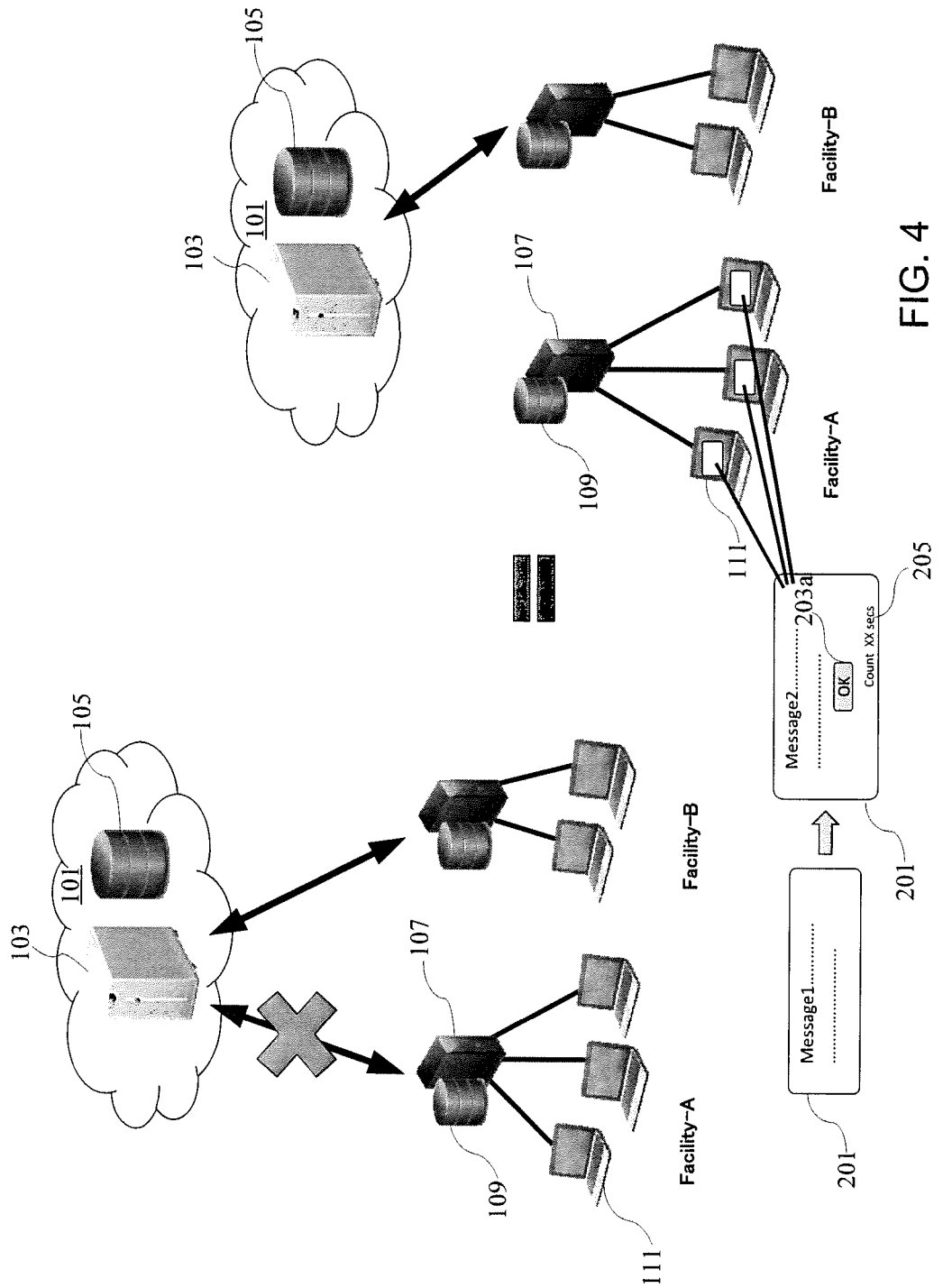
FIG. 4 shows a state of the system of FIGS. 1A and 1B in accordance with one or more embodiments.
Figure 5:
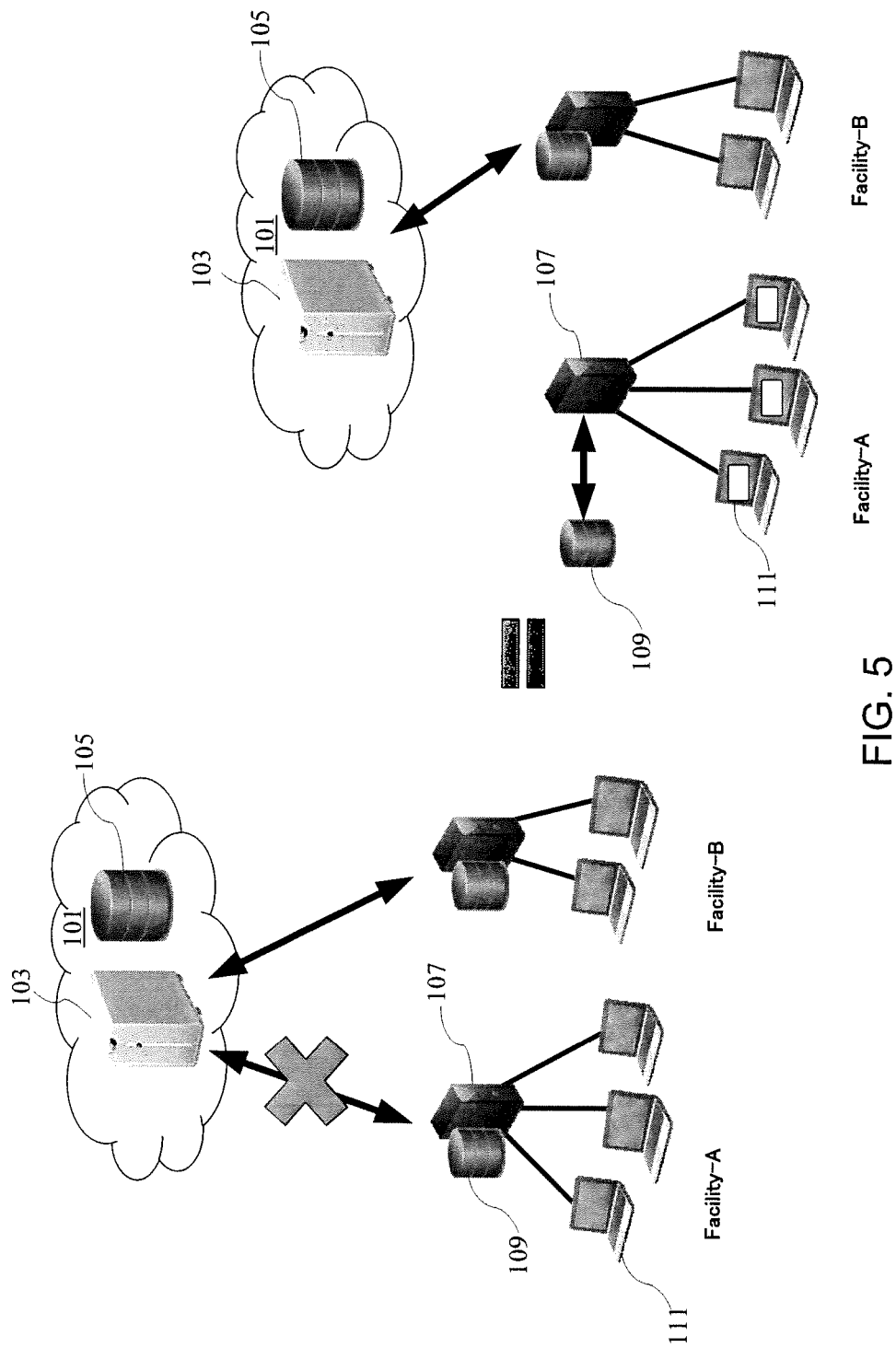
FIG. 5 shows a state of the system of FIGS. 1A and 1B in accordance with one or more embodiments.

FIGS. 4 and 5 each show a state where a connection between a healthcare facility among the multiple in-network healthcare facilities and the cloud (101) gets disconnected. In this case, as shown on the right-hand side of FIG. 4, the local computers (111) associated with the disconnected healthcare facility may first display the display message (201) to indicate that the connection to the cloud (101) is disconnected. The display message (201) may then prompt the user to switch access from the cloud repository (105) to the local repository (109) of the disconnected healthcare facility by selecting the user selectable tab (203a). Additionally or alternatively, the display message (201) may show the user the countdown timer (205) so that the switch will occur automatically once the timer has run out. The right-hand side of FIG. 5 shows the local computers (111) and local servers (107) associated with the disconnected healthcare facility has switched access from the cloud repository (105) to the local repository (109).

Figure 6:
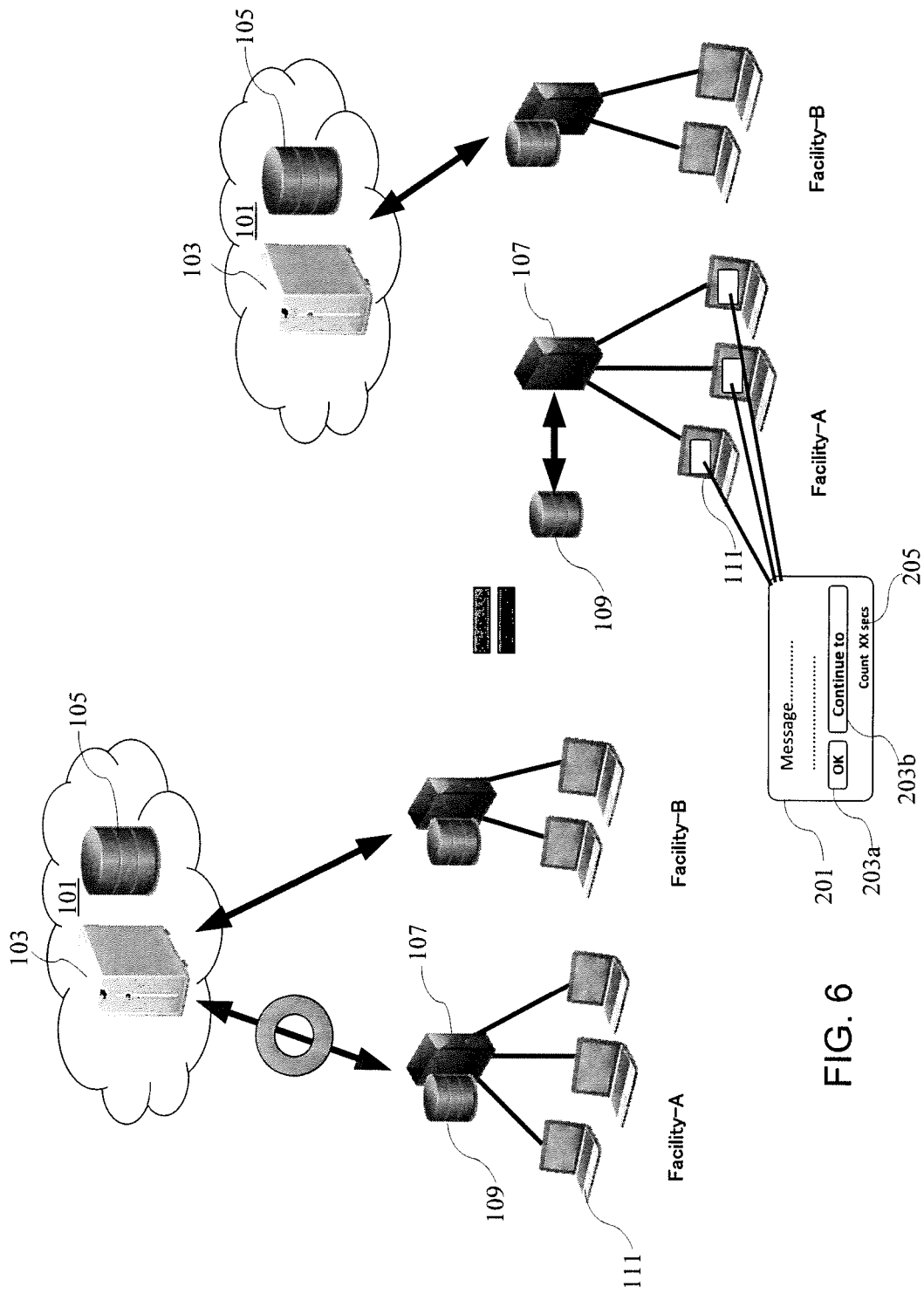
FIG. 6 shows a state of the system of FIGS. 1A and 1B in accordance with one or more embodiments.
Figure 7:
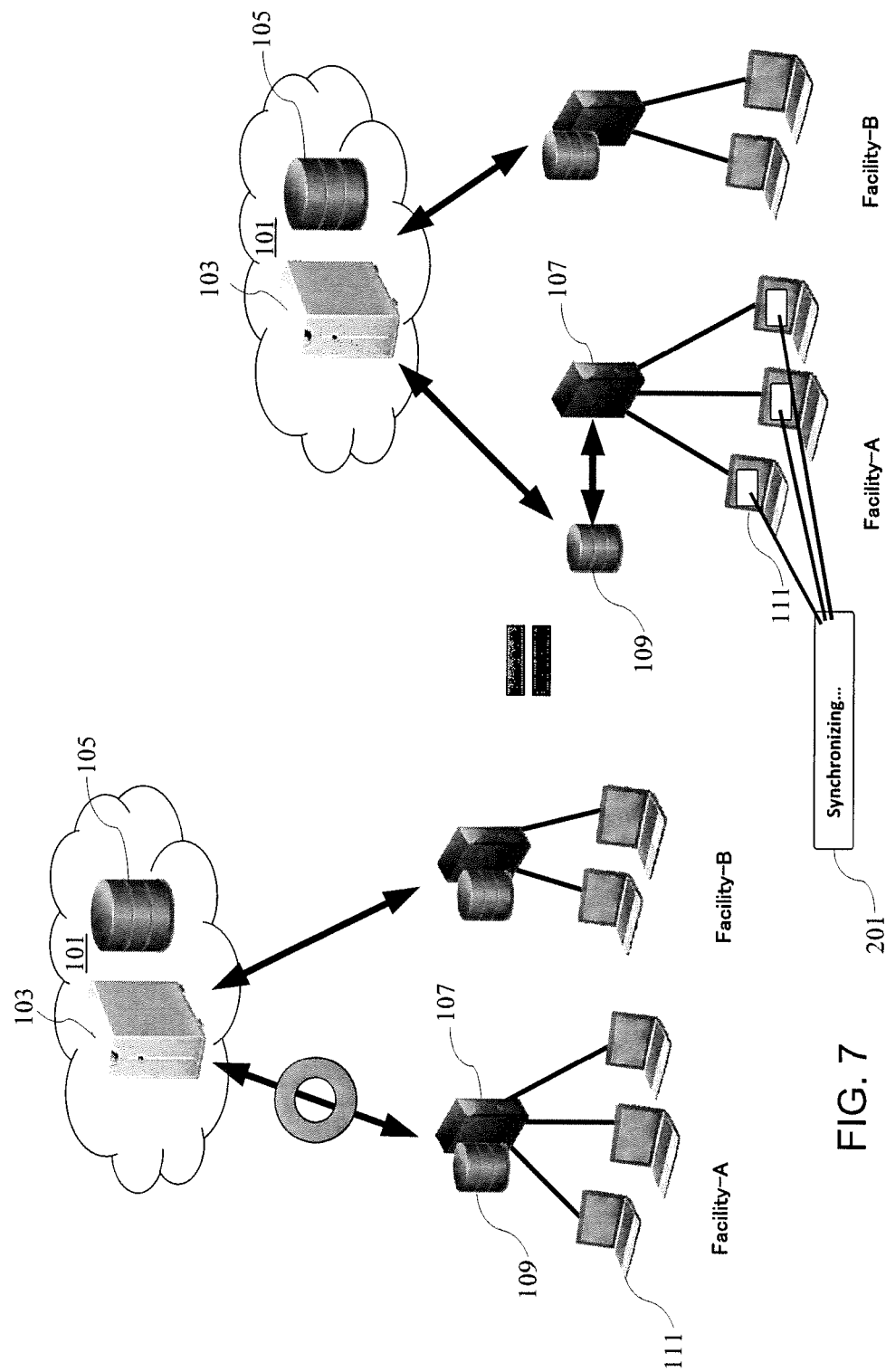
FIG. 7 shows a state of the system of FIGS. 1A and 1B in accordance with one or more embodiments.

FIGS. 6 and 7 each show a state where a connection is reestablished between the disconnected healthcare facility and the cloud (101). In this case, as shown on the right-hand side of FIG. 6, the local computers (111) associated with the re-connected healthcare facility may first display the display message (201) to indicate that the connection to the cloud (101) is re-connected. The display message (201) may then prompt the user to choose between re-accessing the cloud repository (105) (by selecting the user selectable tab (203a)) or continuing to work locally (by selecting the user selectable tab (203b)). Additionally or alternatively, the display message (201) may show the user the countdown timer (205) so that the re-accessing (i.e., switching access from the local repository (109) back to the cloud repository (105)) will occur automatically once the timer has run out. The right-hand side of FIG. 7 shows the local computers (111) associated with the re-connected healthcare facility displaying the display message (201) to indicate that the data stored in the local repository (109) during the time of disconnection is being transmitted to the cloud repository (105), and that the cloud repository (105) is synchronizing with the local repository (109).

Figure 8:
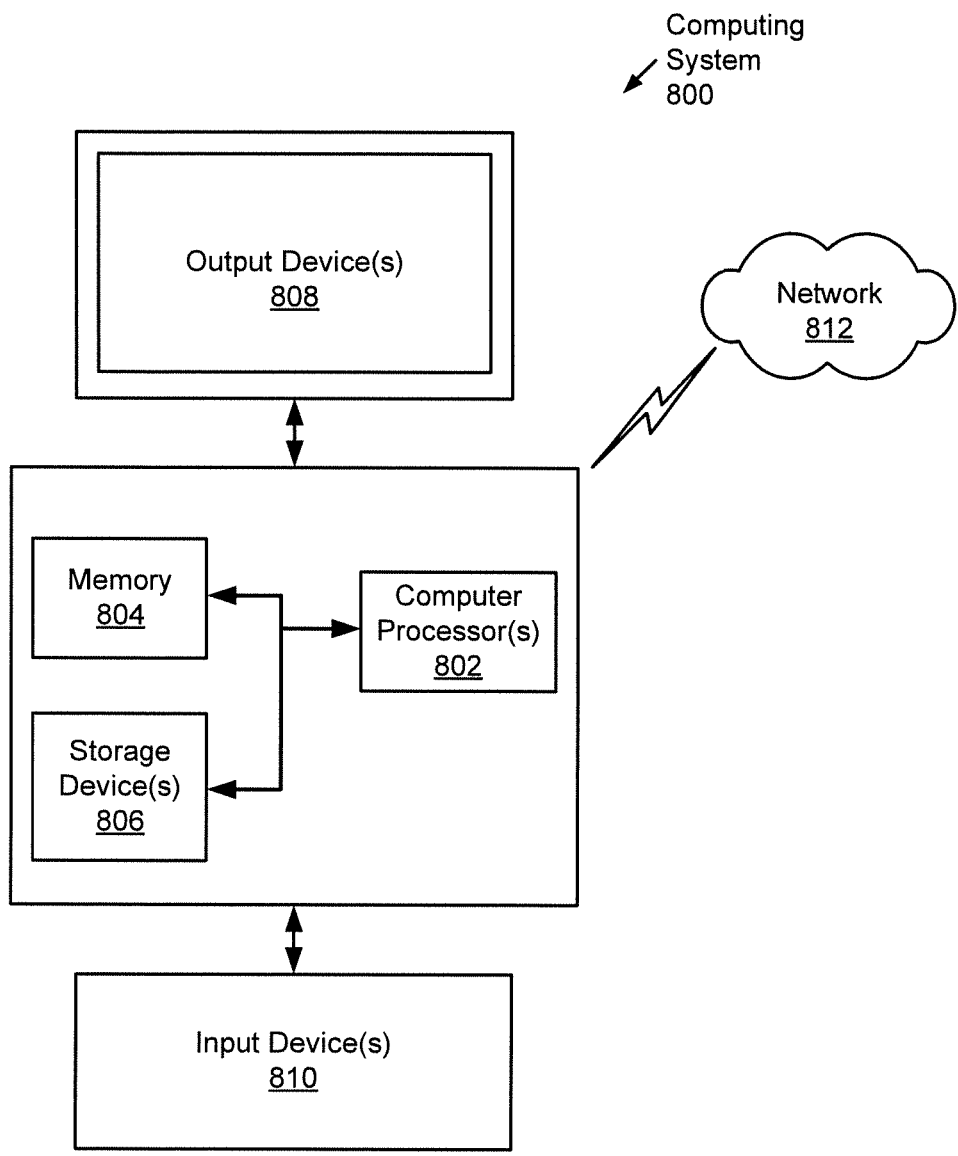
FIG. 8 shows a computing system in accordance with one or more embodiments.

Embodiments of the invention may be implemented on virtually any type of computing system, regardless of the platform being used. For example, the computing system may be one or more mobile devices (e.g., laptop computer, smart phone, personal digital assistant, tablet computer, or other mobile device), desktop computers, servers, blades in a server chassis, or any other type of computing device or devices that includes at least the minimum processing power, memory, and input and output device(s) to perform one or more embodiments of the invention. For example, as shown in FIG. 8, the computing system (800) may include one or more computer processor(s) (802), associated memory (804) (e.g., random access memory (RAM), cache memory, flash memory, etc.), one or more storage device(s) (806) (e.g., a hard disk, an optical drive such as a compact disk (CD) drive or digital versatile disk (DVD) drive, a flash memory stick, etc.), and numerous other elements and functionalities. The computer processor(s) (802) may be an integrated circuit for processing instructions. For example, the computer processor(s) may be one or more cores, or micro-cores of a processor. The computing system (800) may also include one or more input device(s) (810), such as a touchscreen, keyboard, mouse, microphone, touchpad, electronic pen, or any other type of input device. Further, the computing system (800) may include one or more output device(s) (808), such as a screen (e.g., a liquid crystal display (LCD), a plasma display, touchscreen, cathode ray tube (CRT) monitor, projector, or other display device), a printer, external storage, or any other output device. One or more of the output device(s) may be the same or different from the input device(s). The computing system (800) may be connected to a network (812) (e.g., a local area network (LAN), a wide area network (WAN) such as the Internet, mobile network, or any other type of network) via a network interface connection (not shown). The input and output device(s) may be locally or remotely (e.g., via the network (812)) connected to the computer processor(s) (802), memory (804), and storage device(s) (806). Many different types of computing systems exist, and the aforementioned input and output device(s) may take other forms.

Software instructions in the form of computer readable program code to perform embodiments of the invention may be stored, in whole or in part, temporarily or permanently, on a non-transitory computer readable medium such as a CD, DVD, storage device, a diskette, a tape, flash memory, physical memory, or any other computer readable storage medium. Specifically, the software instructions may correspond to computer readable program code that when executed by a processor(s), is configured to perform embodiments of the invention.

Further, one or more elements of the aforementioned computing system (800) may be located at a remote location and connected to the other elements over a network (812). Further, one or more embodiments of the invention may be implemented on a distributed system having a plurality of nodes, where each portion of the invention may be located on a different node within the distributed system. In one embodiment of the invention, the node corresponds to a distinct computing device. Alternatively, the node may correspond to a computer processor with associated physical memory. The node may alternatively correspond to a computer processor or micro-core of a computer processor with shared memory and/or resources.

The computing system of FIG. 8 may include functionality to present raw and/or processed data, such as results of comparisons and other processing. For example, presenting data may be accomplished through various presenting methods. Specifically, data may be presented through a user interface provided by a computing device. The user interface may include a GUI that displays information on a display device, such as a computer monitor or a touchscreen on a handheld computer device. The GUI may include various GUI widgets that organize what data is shown as well as how data is presented to a user. Furthermore, the GUI may present data directly to the user, e.g., data presented as actual data values through text, or rendered by the computing device into a visual representation of the data, such as through visualizing a data model.

For example, a GUI may first obtain a notification from a software application requesting that a particular data object be presented within the GUI. Next, the GUI may determine a data object type associated with the particular data object, e.g., by obtaining data from a data attribute within the data object that identifies the data object type. Then, the GUI may determine any rules designated for displaying that data object type, e.g., rules specified by a software framework for a data object class or according to any local parameters defined by the GUI for presenting that data object type. Finally, the GUI may obtain data values from the particular data object and render a visual representation of the data values within a display device according to the designated rules for that data object type.

Figure 9:
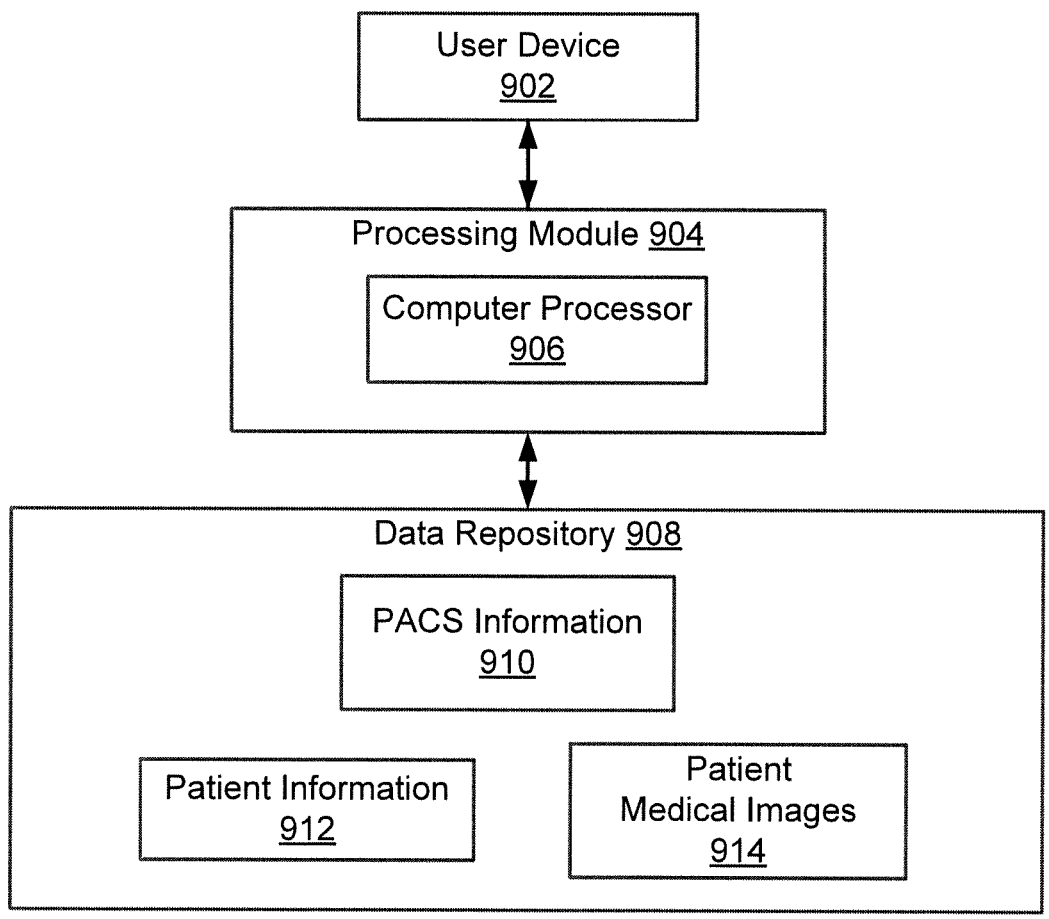
FIG. 9 shows a schematic diagram in accordance with one or more embodiments.

FIG. 9 shows a schematic diagram of a system in accordance with one or more embodiments. The system is configured for synchronizing medical images and data between a cloud repository on a cloud server and a plurality of local repositories on a plurality of local servers connected to the cloud server. The plurality of local servers includes a first local server and the plurality of local repositories includes a first local repository on the first local server. As explained above, the use of ordinal numbers does not imply or create a particular ordering of the elements or limit any element to being only a single element. For example, the "first local server" may be any local server among the plurality of local servers connected to the cloud server, and is merely called "first" for purposes of illustration.

The system as shown in FIG. 9 may include, for example, (i) a processing module (904) including a computer processor (906) configured to execute instructions configured to perform the following steps based on the connection status between the first local server and the cloud server.

In one aspect, in response to a connection between the first local server and the cloud server getting disconnected, the computer processor (906) executes instructions to cause the first local server to (1) access the first local repository instead of the cloud repository, (2) determine whether local data is associated with a shared patient registered with more than one healthcare facility among the healthcare facilities connected to the cloud server, and (3) prohibit alteration of the local data if the local data is associated with the shared patient.

The system as shown in FIG. 9 further comprises (ii) a user device (902) configured to present the medical images and data to a user. The system may further include a data repository (908) configured to store PACS application data (i.e., PACS information) (910) related to the vendor provided application, the patient information (912), and the medical images and data (914).

Figure 10A:
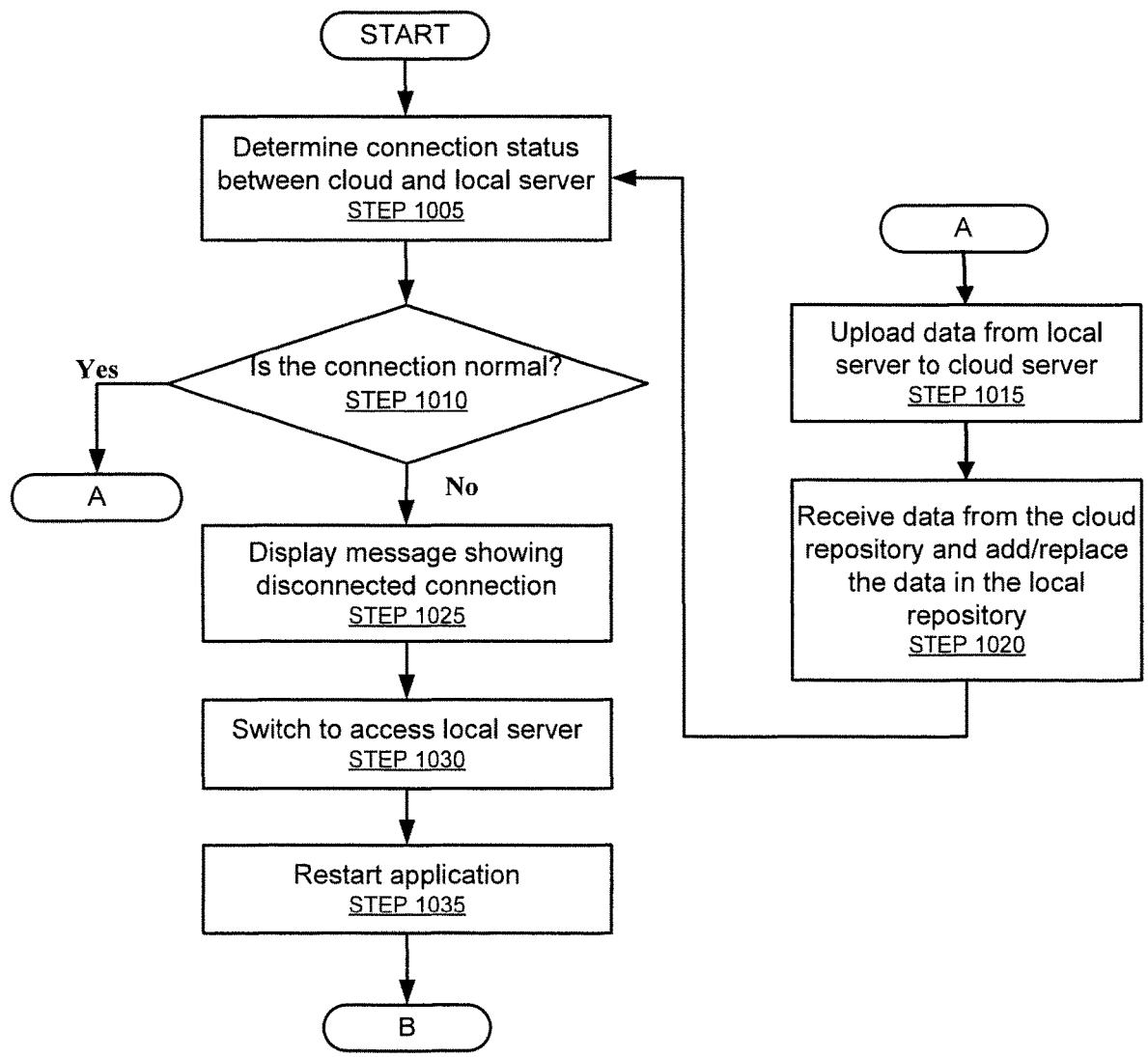
FIGS. 10A and 10B show a flowchart in accordance with one or more embodiments.
Figure 10B:
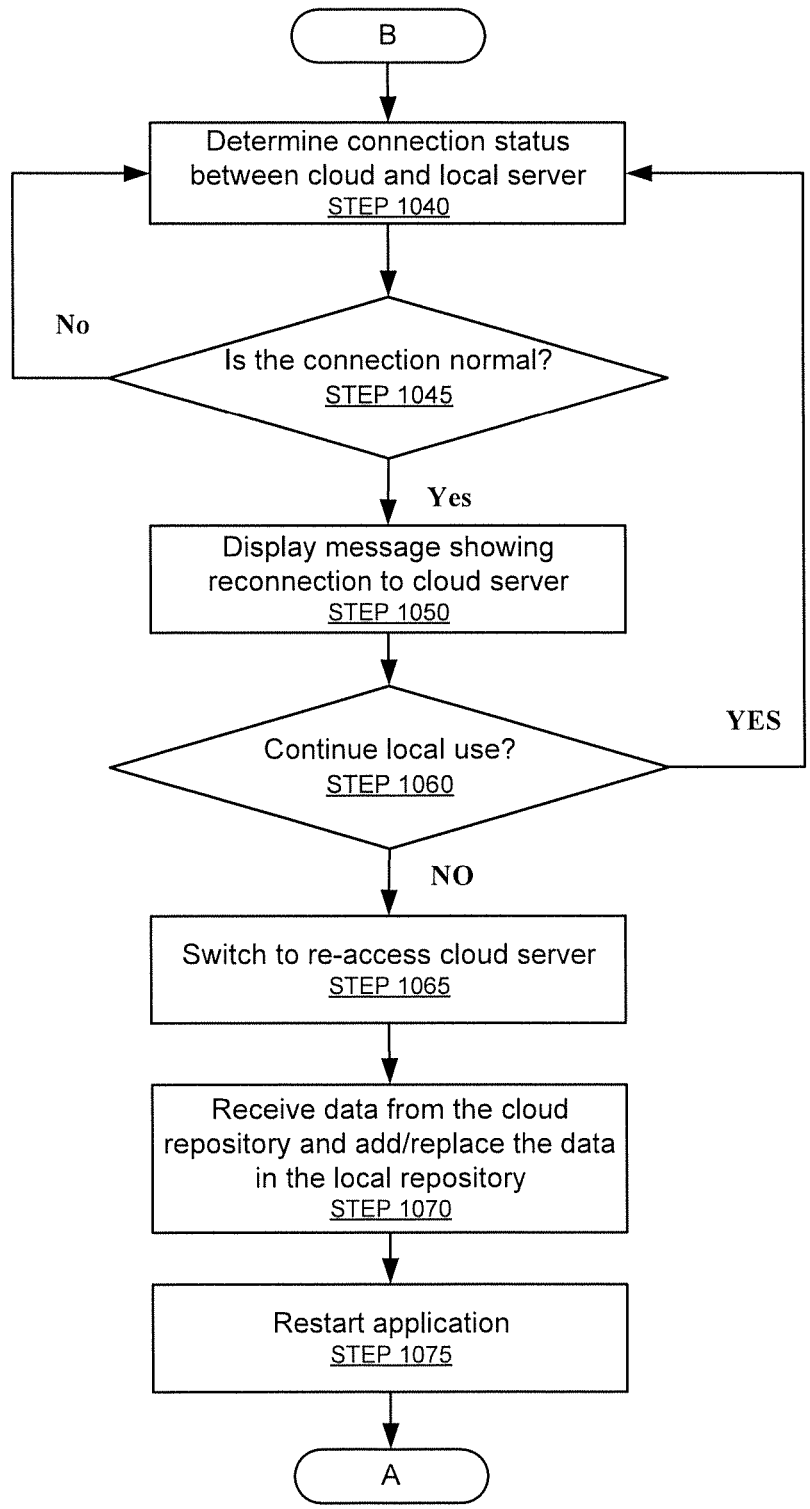

FIGS. 10A and 10B shows a flowchart of a method in accordance with one or more embodiments. In one or more embodiments, the method as shown in FIGS. 10A and 10B is a computer-implemented method. Each step shown in FIGS. 10A and 10B is described together below with respect to only a system of one healthcare facility among the multiple in-network healthcare facilities. It would be apparent to one of ordinary skill in the art that each step of the method described below can be performed by any of the systems of the multiple in-network healthcare facilities.

In Steps 1005 and 1010, the local computers associated with one of the in-network healthcare facilities check the status of the connection between the local servers of the healthcare facility and the cloud server on the cloud to determine if the connection is normal.

If the result of the check in Step 1010 is YES, the local computers continue to upload data generated by the modalities to the cloud server through the local servers in Step 1015, and synchronize a data between the local repositories and the cloud repository in Step 1020. The process then returns to Step 1005.

In one more embodiments, in response to the cloud server being updated in Step 1015, the local computers and servers of the other in-network facilities will receive either all or part of the updated data from the cloud server. When the local computers and servers of the in-network facilities receive the updated data, the respective local computers and servers will either add the updated data to the respective local repositories if the updated data did not previously exist, or replace pre-existing locally-stored data that corresponds to the updated data with the updated data.

If the result of the check in Step 1010 is NO, a message is displayed in Step 1025 to the user indicating that the connection between the healthcare facility and the cloud is disconnected, and that the local computers and servers will be switching access to the local repository (or repositories).

In Step 1030, the local computers and servers of the disconnected healthcare facility switch access to the local repository, and, in Step 1035, an application stored on the local computers and servers that enable the local computers and servers to access the cloud is restarted. At this point, the medical images and data are being stored and retrieved from the local repository instead of from the cloud repository.

In one or more embodiments, when the message is displayed to the users, the users can either click on a user-selectable tab to instantly switch access to the local repository or wait for the local computers and servers to automatically switch access to the local repository when a countdown timer displayed on the message to run out.

In Steps 1040 and 1045, once the application has been restarted, the local computers of the disconnected healthcare facilities perform a check to determine if there is a normal connection between the local servers and the cloud server.

If the result of the check is NO, the local computers and servers continue to operate locally and the process returns to Steps 1040 and 1045 where the local computers check the status of the connection between the local server and the cloud server.

If the result of the check is YES, a message is displayed in Step 1050 to the users indicating that the connection between the healthcare facility and the cloud has been reestablished, and that the local computers and servers are switching access back to the remote repository.

In Step 1060, when the message is displayed to the users, the users are prompted to make a determination if the users want to continue to work locally off the local repository. The local computers and servers will automatically re-access the cloud server if a response by the users is not detected by the time a countdown timer on the message runs out.

If the result of the check is YES, the local computers and servers remain on the local connection for a pre-set period where the local computer continues to check the connection status between the local servers and the cloud server in Step 1040. Once the pre-set time period has expired, the user would be prompted with another display message to reconnect to the cloud. This time, the user would not be able to choose to continue to work locally off the local repository.

If the result of the check is NO, the local computers and servers are configured to re-access the cloud repository in Step 1065.

Then, in Step 1070, when the local computers and servers have re-accessed the cloud repository, the cloud repository is synchronized, i.e., updated with data stored in the local repository during the time of reconnection along with new data that was generated after the reconnection with the cloud server. In the event a conflict has occurred during the disconnection (e.g., when more than one user at different in-network healthcare facilities attempts to simultaneously update the patient information associated with the same remote data on the remote server), the conflict may be resolved automatically by the application or manually by the user through a GUI provided by the application.

In one or more embodiments, a conflict may occur when shared data stored as local data in the local servers of the in-network healthcare facilities are uploaded to the cloud server (e.g., during medical data synchronization between the respective plurality of local servers and the cloud server). For example, the conflict may occur when users at two different in-network healthcare facilities attempt to locally edit or update the same portion of a shared data that is stored as local data at each facility. The shared data is then uploaded from the two facilities to the cloud server. The cloud server will attempt to update the corresponding remote data using the updated shared data received from the two different facilities. When the cloud server tries to update the remote data, the application may not be able to determine which of the updated shared data includes correct patient information, which results in a conflict situation.

More specifically, in one or more embodiments, certain conflict situations may be more complex than others. For example, if a user at in-network healthcare facility A updates a patient name from "AAAAA," to "AAABA," and a user at a different in-network healthcare facility updates the same patient name from "AAAAA," to "AAACA," when the two users attempt to simultaneously update the same remote data to reflect the new patient name, the system will be unable to determine which of the two new names is correct. In this case, the user must manually resolve the conflict. However, if the user at in-network health care facility A edits a patient name from "AAAAA," to "AAABA," and a user at in-network healthcare facility B edits the same patient name from "AAAAA," to "ACAAA," then, when the two users attempt to simultaneously update the same remote data to reflect the new patient name, the application will be able to automatically update the patient name to "ACABA."

Further, the local computers and servers of the disconnected healthcare facility will receive data from the cloud server updated by the other in-network healthcare facilities during the time of disconnection and either add the updated data to the local repository if the updated data did not previously exist, or replace pre-existing locally-stored data that corresponds to the updated data with the updated data.

In one or more embodiments, in response to the cloud server being updated in Step 1070, the local computers and servers of the other in-network facilities will receive either all or part of the updated data from the cloud server. When the local computers and servers of the in-network facilities receive the updated data, the respective local computers and servers will either add the updated data to the respective local repositories if the updated data did not previously exist, or replace pre-existing locally-stored data that corresponds to the updated data with the updated data.

In Step 1075, when all of the data stored in the local repository during the time of reconnection is transmitted to the cloud repository, the application is restarted and local computers are configured to return to Step 1005.

Figure 11A:
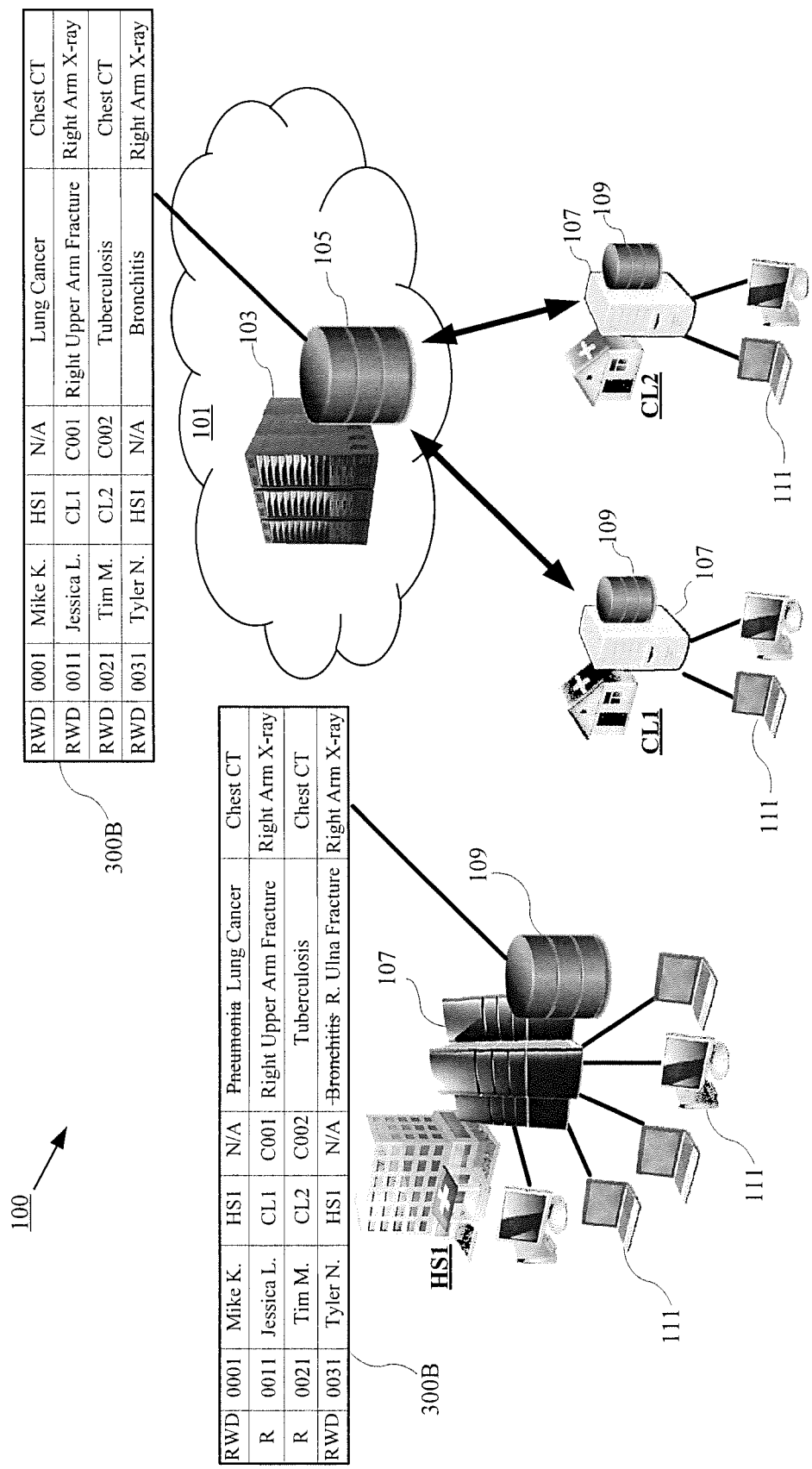
FIGS. 11A and 11B show a state of the system of FIGS. 1A and 1B in accordance with one or more embodiments.
Figure 11B:
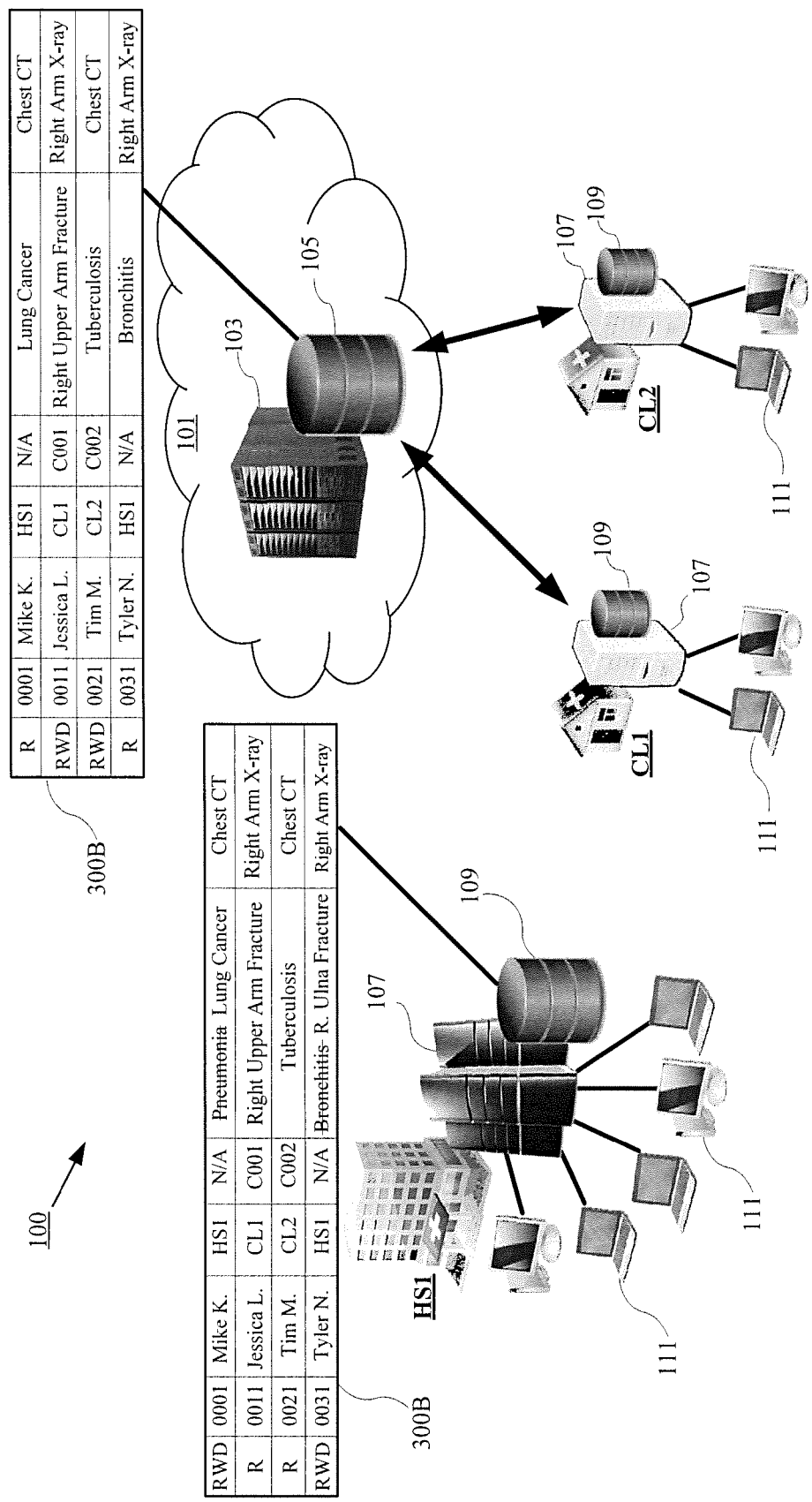

In accordance with one or more embodiments, FIGS. 11A and 11B show the Edit Status (304) of the metadata during a state of the system of FIGS. 1A and 1B where one of the multiple in-network healthcare facilities is disconnected from the cloud server (103) on the cloud (101). It would be apparent to one or ordinary skill in the art the same concept would apply to a state where more than one facility is disconnected from the cloud.

FIG. 11A shows an example in accordance with one or more embodiments where the system (100) includes three facilities: Hospital 1 (HS1), Clinic 1 (CL1), and Clinic (CL2). The local computers (111) coupled to the local server (107) disposed at HS1 are disconnected from the cloud server (103), while the local computers (111) coupled to the respective local servers (107) of CL1 and CL2 are connected to the cloud server (103).

In one or more embodiments as shown in FIG. 11A, not all of the medical data stored as local data in the local server (109) of disconnected HS1 can be edited by the local computers (111) at HS1. For example, as shown in the data table (300B) associated with the local server (109) of HS1, which includes information of all medical data stored locally in the local server (109) of HS1, the local data for patients "Jessica L." and "Tim M." (i.e., the shared patients) cannot be edited while the local computers (111) at HS1 are disconnected from the cloud server (103). The medical data of the shared patients stored in the local repository (109) of HS1 are labeled with the Edit Status (304) "R" to indicate that these medical data are "Read Only" data that cannot be edited. In one or more embodiments as shown in FIG. 11A, all of the remote data stored in the cloud server (103) can be edited by the users at the other in-network healthcare facilities that have active connections with the cloud (101).

In one or more embodiments, the local computers (111) at HS1 prohibit alteration of local data that include a Common Patient ID (306), which indicates that the local data is associated with a shared patient. Further, the local data for the shared patients also include Attributed Facility IDs (305) "CL1" and "CL2", respectively, that indicate that the original medical data was not obtained at HS1.

In one or more embodiments, because the same medical data for the shared patients may be stored locally in the local servers (109) of CL1 and CL2, respectively, users at disconnected HS1 have no easy way of knowing whether users at CL1 or CL2 are editing their respective local versions of the shared data. Therefore, users at CL1 and CL2 might upload the edited local data for the shared patients at the same time the local computers (111) at HS1 are synchronizing the local server (109) with the cloud sever (103) upon reconnection, which would result in a conflict.

Referring still to FIGS. 11A and 11B, users at CL1 and CL2 may not know that HS1 is disconnected from the cloud (101). A user at CL1 may be viewing the remote data on the cloud server (103) and notice a typographical error in a remote data associated with disconnected HS1. The user at CL1 may then correct the typographical error by modifying that specific remote data without knowing that the local computers (111) of HS1 have reestablished connection with the cloud (101) and are in the process of synchronizing medical data with the cloud server (103). This results in a conflict because the remote data was simultaneously edited and updated in the cloud server (103) by two different users at different in-network healthcare facilities.

In one of more embodiments, to further reduce the possibility of conflict when a disconnected healthcare facility synchronizes local data with the cloud (101) upon reconnection as described above, a limitation is placed upon the remote data that can be modified when one of the multiple in-network healthcare facilities is disconnected. For example, as shown in FIG. 11B, the users at CL1 and CL2, which are still connected with the cloud (101), are prohibited from editing the remote data on the cloud server (103) that are associated with disconnected HS1.

Figure 12:
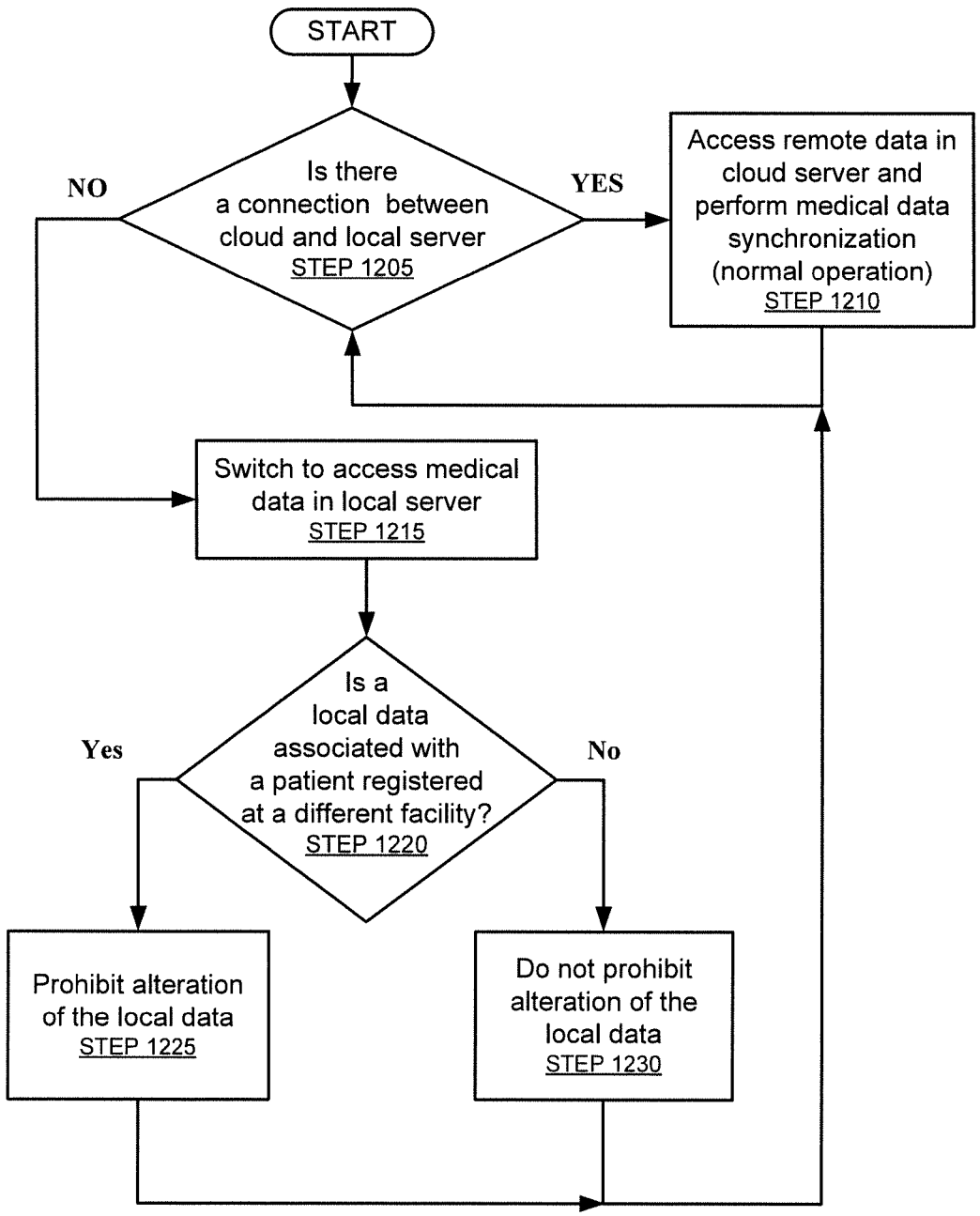
FIG. 12 shows a flow chart in accordance with one or more embodiments.

FIG. 12 shows a flowchart of a method in accordance with one or more embodiments. In one or more embodiments, the method as shown in FIG. 12 is a computer-implemented method. Each step shown in FIG. 12 is described together below with respect to only a system of one healthcare facility among the multiple in-network healthcare facilities. It would be apparent to one of ordinary skill in the art that each step of the method described below can be performed by any of the systems of the multiple in-network healthcare facilities.

In Step 1205, the local computers associated with one of the in-network healthcare facilities check the status of the connection between the local servers of the healthcare facility and the cloud server on the cloud to determine whether the connection is normal similar to Steps 1005 and 1010 as of flow charts of FIGS. 10A and 10B.

If the result of the check in Step 1205 is YES, the method proceeds to Step 1210 where the local computers access the medical data in the cloud server and perform normal operation as described in Steps 1015 and 1020 of the flow charts of FIGS. 10A and 10B.

If the result of the check in Step 1205 is NO, the method proceeds to Step 1215 where the local computers and local servers of the disconnected healthcare facility switch access to the local repository. In one or more embodiments, a message is displayed to the users and the application is restarted, similar to Steps 1025 and 1035 as described in the flow charts of FIGS. 10A and 10B.

In Step 1220, while the local computers and local servers are disconnected from the cloud server, a determination is made by the local computers and local servers whether each of the local data stored in the local repository is a shared data.

If the result of the determination in Step 1220 is YES for a particular local data among the local data stored in the local repository, the method proceeds to Step 1225 where the first local computer will prohibit the user from altering (i.e., making any modifications or edits) that particular local data determined to be shared data.

If the result of the determination in Step 1220 is NO for a particular local data among the local data stored in the local repository, the method proceeds to Step 1230 where the first local computer will not prohibit the user from altering that particular local data determined as not being shared data.

FIGS. 13A, 13B, and 13C show an implementation example in accordance with one or more embodiments. As shown in FIGS. 13A, 13B, and 13C each of the functional items are broken down into a large item ("a top-level function") and multiple small items ("sub-functions of the top-level functions"). The top-level functions and the sub-functions are implemented by a user or a respective component of the system shown in FIGS. 1A and 1B during each step of the flowchart as shown in FIGS. 10A, 10B, and 12.

According to one or more embodiments, the contents of each sub-function describe the actions that can be implemented by the user or the respective components of the system shown in FIGS. 1A and 1B when each sub-function is being implemented. The actions also show the actions that cannot be implemented by the user when a specific sub-function is being implemented.

According to one or more embodiments, the settings describe a user-set interval or amount of time associated with specific sub-functions that may be repeated or set with a specific time restriction when implements. The settings may be non-configurable settings that are pre-set by the vendor that provides the application. Further, the settings may be user-configurable settings that can be configured by a user with high administrative authority in the healthcare facility.

One or more embodiments of the invention may have one or more of the following advantages: the ability to automatically share and update medical images and data between multiple healthcare facilities that are in-network; the ability to maintain all of the local repositories of all of the in-network healthcare facilities that serve the same individual up-to-date with the individual's most recent medical images and data; the ability to establish a continuous workflow at every in-network healthcare facility without experiencing any downtime caused by a disconnection of any of the in-network healthcare facility with the share cloud; the ability to select the medical images and data to be stored in the local repositories of the respective in-network healthcare facilities so that the healthcare facilities would not need to maintain a full-sized on-site data center; the ability to reduce the possibility of conflict, by users at an in-network healthcare facility that is disconnected with the cloud, when the disconnected in-network healthcare facility synchronizes medical data between a local server and a cloud server upon reconnection to the cloud; the ability to reduce the possibility of conflict, by users at in-network healthcare facilities that are still connected with the cloud, when an in-network healthcare facility that was disconnected with the cloud synchronizes medical data between a local server and a cloud server upon reconnection to the cloud; etc.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method to prevent conflict during synchronization of medical data between a cloud repository on a cloud server and a local repository on a local server, the method comprising:
    detecting a loss of connection between the local server and the cloud server;
    accessing the local repository and blocking access to the cloud repository;
    determining, based on presence/absence of a common patient ID in metadata stored in local data, that:
        the local data is associated with a shared patient registered with other local servers that are connected to the cloud server, or
        the local data is not associated with the shared patient;
    preventing the local server from updating or deleting the local data after determining that the local data is associated with the shared patient, while not preventing the other local servers from updating or deleting any remote data that is stored in the cloud repository and that corresponds to the local data;
    detecting that the connection between the local server and the cloud server is established;
    after detecting that the connection between the local server and the cloud server is established,
        receiving, from the cloud repository, remote data sent from other local servers to the cloud repository;
        replacing local data with the remote data when the remote data updates the local data; and
        storing the remote data in the local repository as new local data when the remote data does not update any of local data in the local repository;
    detecting that the connection between the local server and the cloud server was lost and reestablished;
    after detecting the connection between the local server and the cloud server was lost and is restored,
        receiving remote data that was updated while the connection was lost;
        replacing local data with the remote data when the remote data updates the local data; and
        storing the remote data in the local repository as new local data when the remote data does not update any of local data in the local repository; and
    sending any local data on the local repository that was updated or added while the connection was lost to the cloud repository.

2. The method according to claim 1, further comprising: not preventing the local server from updating or deleting local data associated with the shared patient after detecting the connection between the local server and the cloud server is reestablished.

3. The method according to claim 1, further comprising: after detecting the loss of the connection between the local server and cloud server, adding new medical data associated with the shared patient as new local data in the local repository.

4. The method according to claim 1, wherein determining that the local data is associated or not associated with the shared patient is performed based on information from metadata stored in the local data.

5. The method according to claim 4, wherein
    the metadata stored in the local data includes a patient ID, a patient name, an attributed facility ID a patient report information, an image information, and an editing status identifier,
    the attributed facility ID is an identification of a healthcare facility that generates data associated with the shared patient, and
    the common patient ID indicates that a patient is shared between two or more healthcare facilities or that the patient is not shared.

6. The method according to claim 5, wherein the metadata of the local data is editable by a user through a graphical user interface (GUI) displayed by a computer coupled to a plurality of local servers that includes the local server.

7. The method according to claim 6, wherein the local server determines that the local data is associated or not associated with the shared patient based on the common patient ID in the metadata.

8. The method according to claim 1, wherein the medical data is a DICOM-format image or a patient's medical report.

9. The method according to claim 8, wherein the DICOM-format image is a medical image taken using a modality in a medical facility connected to a computer coupled to a plurality of local servers.

10. The method according to claim 1, wherein the local server is coupled to a local computer.

11. The method according to claim 1, wherein the cloud repository on the cloud server is a repository for a cloud-based Picture Archiving and Communication System (PACS).

12. The method according to claim 1, further comprising:
    not preventing the local server from updating or deleting the local data that is not associated with the shared patient.

13. A non-transitory computer-readable medium (CRM) storing instructions that performs an operation to prevent conflict during synchronization of medical data a between a cloud repository on a cloud server and a local repository on a local server, the operation comprising:
    detecting a loss of connection between the local server and the cloud server;
    accessing the local repository and blocking access to the cloud repository;
    determining, based on presence/absence of a common patient ID in metadata stored in local data, that:
        the local data is associated with a shared patient registered with other local servers that are connected to the cloud server, or
        the local data is not associated with the shared patient;
    preventing the local server from updating or deleting the local data after determining that the local data is associated with the shared patient, while not preventing the other local servers from updating or deleting any remote data that is stored in the cloud repository and that corresponds to the local data;
    detecting that the connection between the local server and the cloud server is established;
    after detecting that the connection between the local server and the cloud server is established,
        receiving, from the cloud repository, remote data sent from the other local servers to the cloud repository;
        replacing local data with the remote data when the remote data updates the local data; and
        storing the remote data in the local repository as new local data when the remote data does not update any of local data in the local repository;

detecting the connection between the local server and the cloud server was lost and is reestablished;

after detecting the connection between the local server and the cloud server was lost and is restored, receiving remote data that was updated while the connection was lost;

replacing local data with the remote data when the remote data updates the local data; and storing the remote data in the local repository as new local data when the remote data does not update any of local data in the local repository; and sending any local data on the local repository that was updated or added while the connection was lost to the cloud repository.

14. The CRM according to claim 13, wherein the operation further comprises: not preventing the local server from updating or deleting local data associated with the shared patient after detecting the connection between the local server and the cloud server is reestablished.

15. The CRM according to claim 13, wherein the operation further comprises:

after detecting the loss of the connection between the local server and cloud server, adding new medical data associated with the shared patient as new local data in the local repository.

16. A system that prevents conflict during synchronization of medical data, comprising:

a cloud server;

a cloud repository on the cloud server;

a local server; and a local repository on the local server; wherein the local server:

detects a loss of connection between the local server and the cloud server;

accesses the local repository and blocks access to the cloud repository;

determines, based on presence/absence of a common patient ID in metadata stored in local data, that:

the local data is associated with a shared patient registered with other local servers that are connected to the cloud server, or the local data is not associated with the shared patient; and is prevented from updating or deleting the local data after determining that the local data is associated with the shared patient, while the local server is not prevented from updating or deleting any remote data that is stored in the cloud repository and that corresponds to the local data, after the local server detects that the connection between the local server and the cloud server is established, the local server:

receives, from the cloud repository, remote data sent from the other local servers to the cloud repository;

replaces local data with the remote data when the remote data updates the local data; and stores the remote data in the local repository as new local data when the remote data does not update any of local data in the local repository;

after the local server detects the connection between the local server and the cloud server was lost and is reestablished, the local server:

receives remote data that was updated while the connection was lost;

replaces local data with the remote data when the remote data updates the local data;

stores the remote data in the local repository as new local data when the remote data does not update any of local data in the local repository; and sends any local data on the local repository that was updated or added while the connection was lost to the cloud repository.

17. The system according to claim 16, wherein the system does not prevent the local server from updating or deleting local data associated with the shared patient after the local server detects the connection between the local server and the cloud server is reestablished.

18. The system according to claim 16, wherein the local server detects the loss of the connection between the local server and cloud server, the local server adds new medical data associated with the shared patient as new local data in the local repository.

* * * * *